United States Patent [19]
Allington et al.

[11] Patent Number: 5,169,511
[45] Date of Patent: Dec. 8, 1992

[54] CAPILLARY ELECTROPHORESIS TECHNIQUE

[75] Inventors: Robert W. Allington; John R. Allington, both of Lincoln, Nebr.

[73] Assignee: Isco, Inc., Lincoln, Nebr.

[21] Appl. No.: 469,311

[22] Filed: Jan. 24, 1990

Related U.S. Application Data

[63] Continuation-in-part of Ser. No. 277,566, Nov. 29, 1988.

[51] Int. Cl.$^5$ .................. G01N 27/26; B01D 57/02
[52] U.S. Cl. ......................... 204/299 R; 204/180.1
[58] Field of Search .................... 204/180.1, 299 R

[56] References Cited

U.S. PATENT DOCUMENTS

| | | | |
|---|---|---|---|
| 4,911,807 | 3/1990 | Burd | 204/180.1 |
| 5,045,174 | 9/1991 | Guzman | 204/299 R |

OTHER PUBLICATIONS

Donald J. Rose, Jr. & James W. Jorgenson "Characterization and Automation of Sample Introduction Methods for Capillary Zone Electrophoresis" Analytical Chemistry, 60, (1988), 642–648.

Donald J. Rose, Jr. & James W. Jorgenson, "Fraction Collector for Capillary Zone Electrophoresis" Journal of Chromatography 438 (1988) 23–34.

*Primary Examiner*—John Niebling
*Assistant Examiner*—John S. Starsiak, Jr.
*Attorney, Agent, or Firm*—Vincent L. Carney

[57] ABSTRACT

To collect from an electrophoresis capillary tube containing a liquid separating medium, a sample cup has two wells containing electrolyte. The bottoms of the wells are covered with clamped-on semipermeable membrane assemblies to permit the flow of buffer ions but not the migration of separated sample. Electrical continuity for the electrophoretic migration taking place in capillary tubes is provided through the electrolyte in wells, the assembled semipermeable membranes, electrolyte buffer residing the carrier, the electrode and a conductor leading to electrical ground. Separated zones are detected, electrophoretically eluted or electrosmotically discharged from the capillary tube into the electrolyte in well where they are trapped by the semipermeable membrane in assembly.

45 Claims, 12 Drawing Sheets

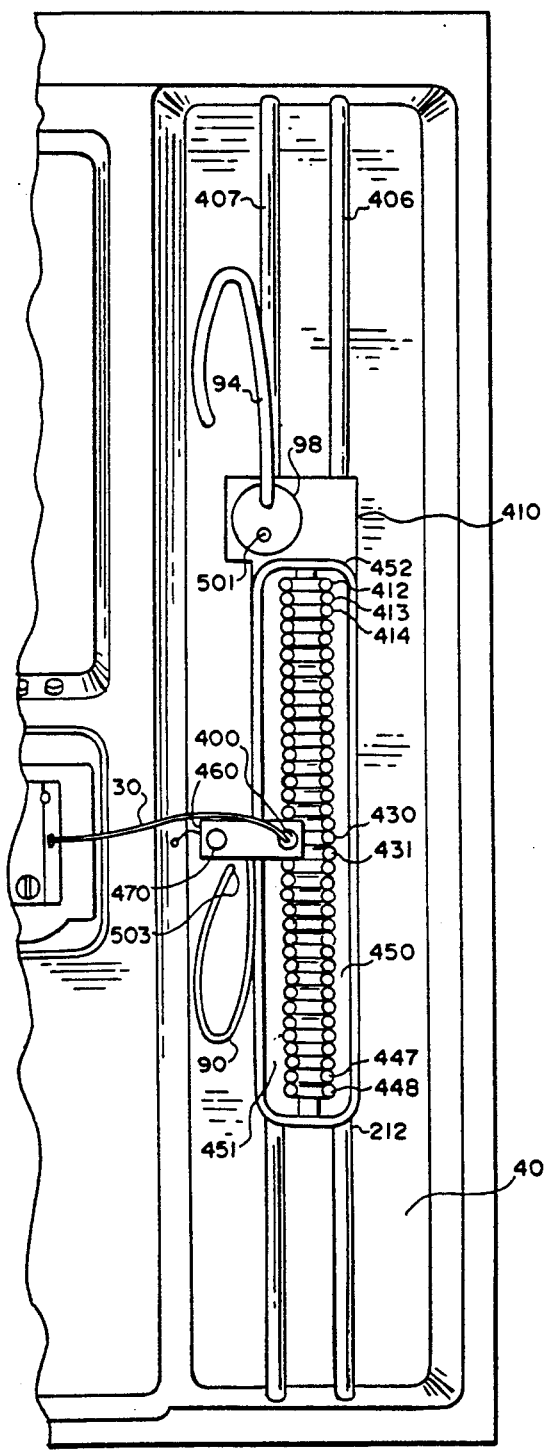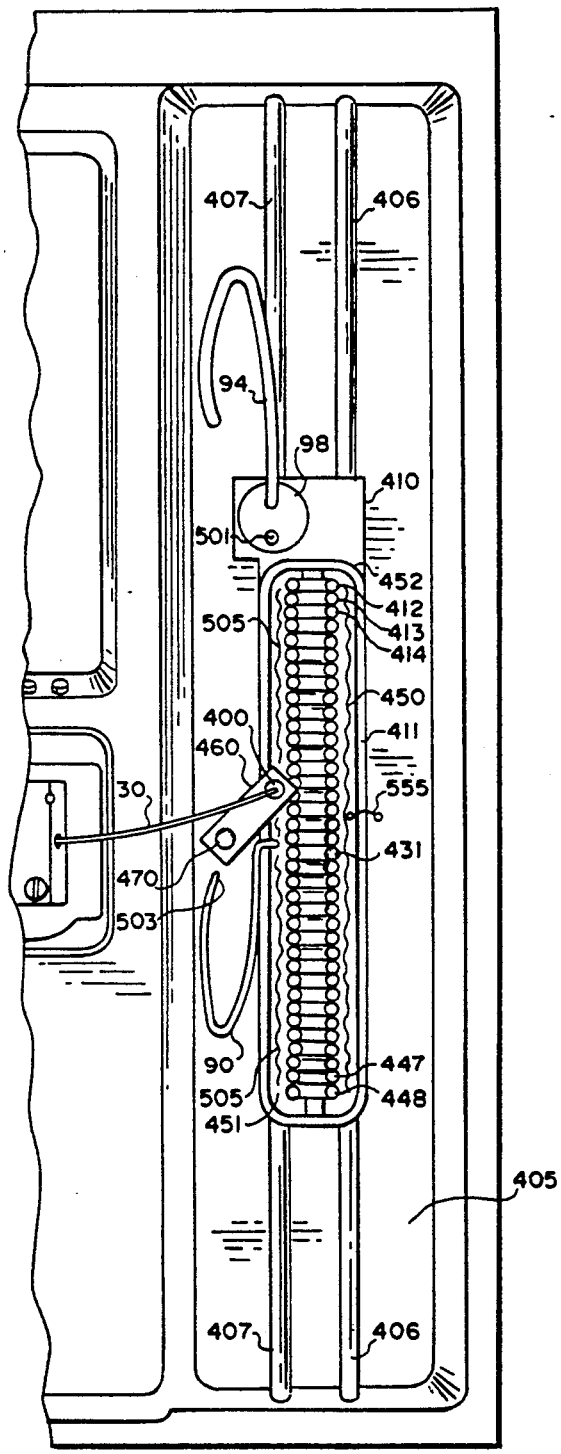

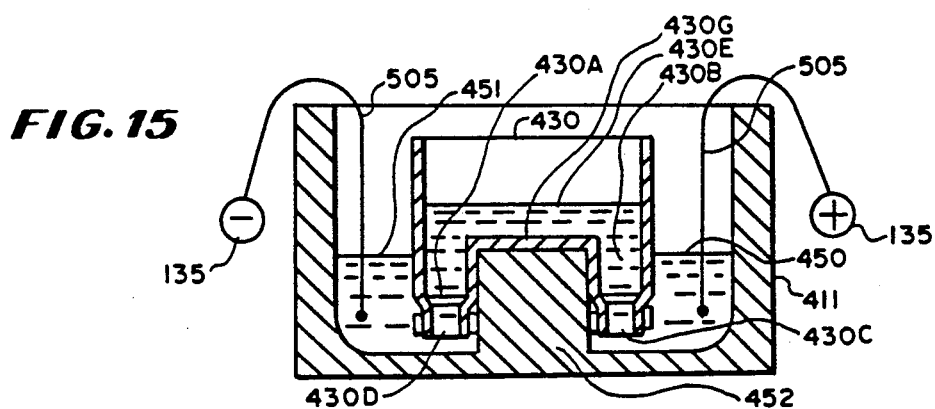
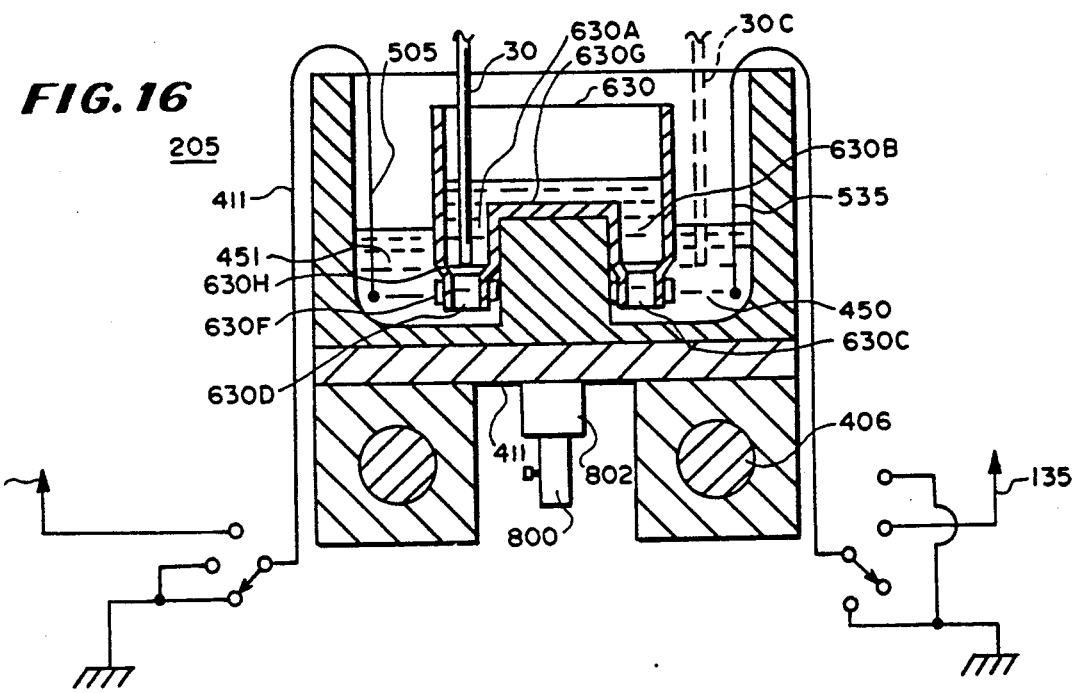
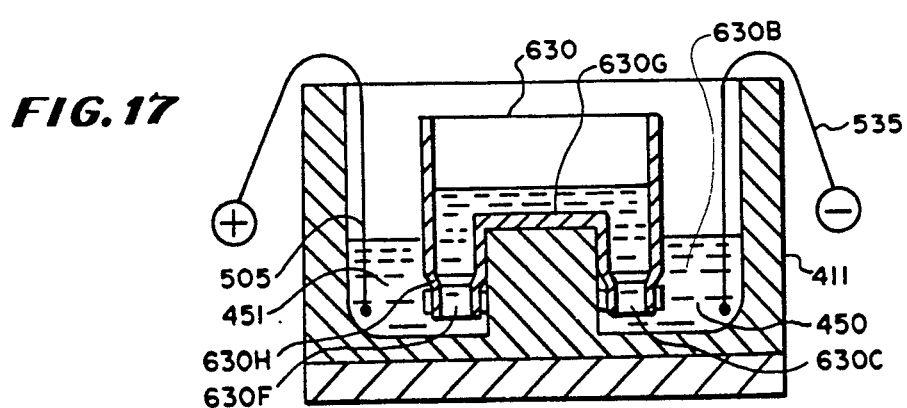

CAPILLARY ELECTROPHORESIS TECHNIQUE

RELATED CASES

This application is continuation-in-part of United States application Ser. No. 277,566 filed Nov. 29, 1988, in the name of Robert William Allington and assigned to the same assignee as this application.

BACKGROUND OF THE INVENTION

This invention relates to techniques in the separation sciences and more particularly to techniques for collecting separated sepcimen, such as for example, the type of collecting performed by apparatus known as fraction collectors.

It is known in the separation sciences to automatically collect materials separated by a separating apparatus. One type of such separating apparatus performs separation by electrophoresis and is known as an electrophoresis apparatus. In this process, the samples are separated in a medium as the molecular species are moved through the medium under the influence of an electrical potential.

One class of electrophoresis apparatus is a capillary electrophoresis apparatus. In a capillary electrophoresis apparatus, the medium is in a small diameter capillary tube. This tube is usually made of fused quartz. The electrophoresis medium may be a gel or liquid in capillary electrophoresis. The separated bands or zones of molecular species are sensed by a detector that transmits light through the medium and senses the species as they move along the medium by differences in absorbance of the light. The volume of such zones is low, such as for example, 20 nanoliters.

Fraction collection such as a rotation table with containers on it have been used to collect separated fractions from separating devices. However, such prior art fraction collectors are not easily used for collecting fractions from capillary electrophoresis apparatuses for further use after initial absorbance detector assay because of the small volume of the sample components or zones within the capillary tube. Because the sample concentration within the zone may already be low, further dilution in the fraction collection process should be avoided. This is difficult to do as both the electrical ground connection and the capillary tube are immersed in a collecting electrolyte necessary to provide electrical continuity. This volume of electrolyte further dilutes the sample zone.

SUMMARY OF THE INVENTION

Accordingly, it is an object of the invention to provide novel techniques for use in the separation sciences.

It is a further object of the invention to provide a novel fraction collector in the separation sciences.

It is a still further object of the invention to provide a novel fraction collector suitable for use in collecting effluent from capillary separation procedures such as capillary electrophoresis and capillary chromatography.

It is a still further object of the invention to provide a novel technique for collecting fractions of low volume without excessive dilution.

It is a still further object of the invention to provide a technique for collecting fractions from electrophoresis and concentrating them in a trap.

In accordance with the above and further objects of the invention, a capillary electrophoresis apparatus includes a capillary tube, a means for injecting samples into the tube, a means for applying a potential across the tube and a fraction collector adapted to receive fractions of one or more zones detected by the electrophoresis apparatus in separate containers, with the source of potential being adapted to be applied to the end of the tube within the different containers of the fraction collector. Advantageously, the separate containers of the fraction collector are capable of concentrating the samples and a plurality of different containers are in a carrier which may be easily removed from the electrophoresis apparatus as a group.

In one embodiment, a removable carrier includes a buffer liquid and a plurality of sample concentrating cells so that individual fractions of one or more zones are deposited in one side of the concentrating cells. At a later time, a potential may be applied between different portions of the cell to move the sample to a concentrating location where it is concentrated against a membrane. The concentrating step may be performed either within the electrophoresis apparatus or outside of the electrophoresis apparatus. In another embodiment, a salt trap is used which receives the sample in a buffer above a higher density salt solution as the fractions are collected and then, the salt cell has a potential applied which causes concentration of the sample on the high density salt layer.

From the above description, it can be understood that the electrophoresis apparatus of this invention has several advantages, such as for example: (1) it is capable of collecting the relatively small volumes of zones from capillary electrophoresis; (2) sample does not plate out on electrodes of the electrophoresis apparatus but is plated into a buffer but yet is not unduly diluted; (3) the sample may be conveniently concentrated in the fraction collector; (4) the sample containers are conveniently handled and may be removed from the electrophoresis apparatus for concentrating or storage in another carrier with sample containers inserted; and (5) eluent that is unfavorably affected by contact with membranes may be concentrated on high density salt layers in a salt trap as part of the collection process.

SUMMARY OF THE DRAWINGS

The above noted and other features of the invention will be better understood from the following detailed description when considered with reference to the accompanying drawings, in which:

FIG. 13 is an enlarged fragmentary plan view of a portion of the fraction collector of FIG. 1;

FIG. 14 is an enlarged fragmentary plan view of a portion of the fraction collector of FIG. 1;

FIG. 15 is a fragmentary schematic sectional view of a sample collecting and concentrating cup and fraction collector as used for the reconcentration of samples in a membrane trap after their dilution during the initial fraction collection process;

FIG. 16 is a fragmentary schematic sectional view of another embodiment of sample collecting and concentrating cup altered to include a novel salt trap for fraction collection;

FIG. 17 is a fragmentary schematic sectional view of another embodiment of sample collecting and concentrating cup as connected for the reconcentration of samples in a novel salt trap after the initial fractionation process;

DETAILED DESCRIPTION

Figure 1:
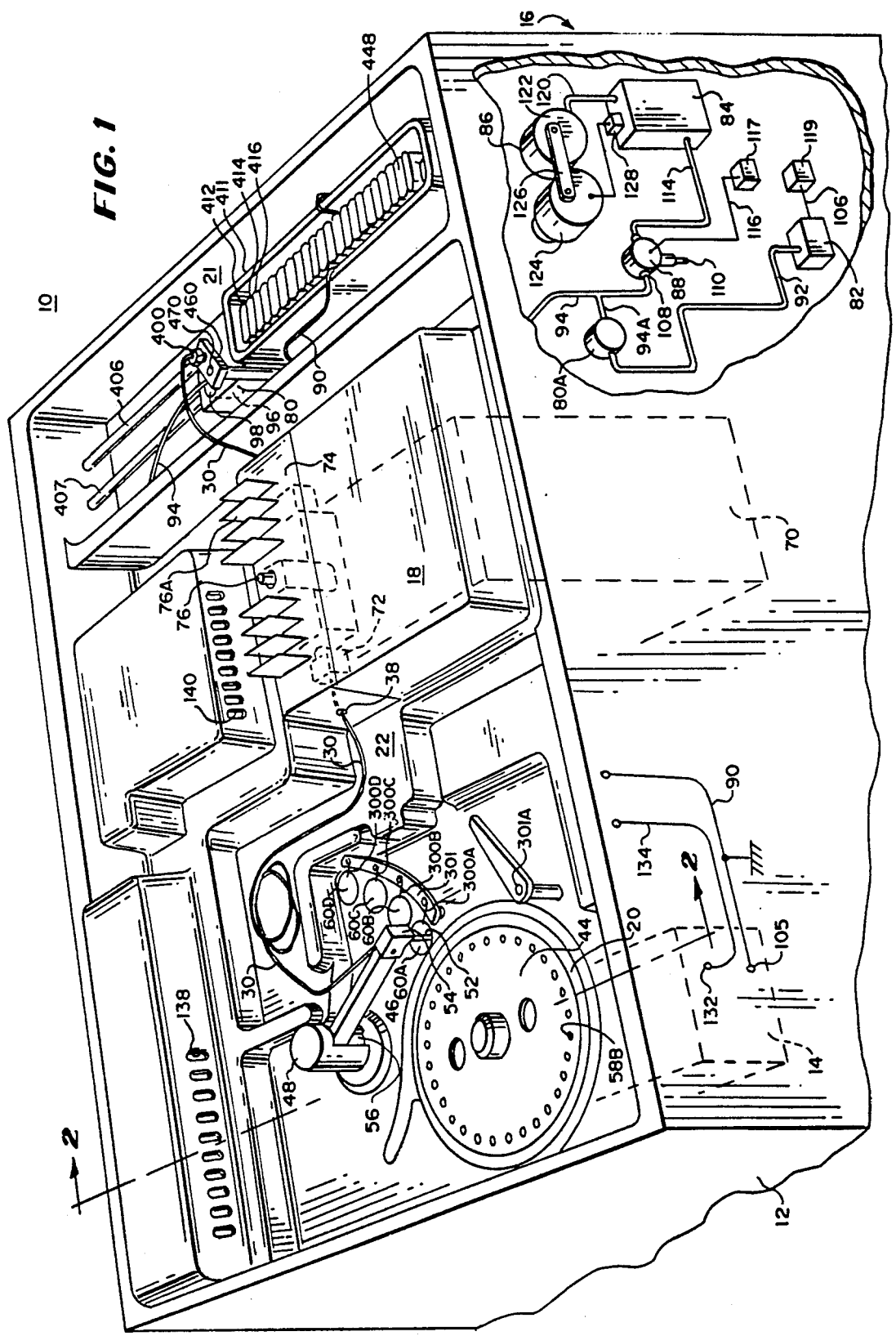
FIG. 1 is a simplified perspective view of an electrophoresis apparatus according to the invention including a sample collecting mechanism.

In FIG. 1, there is shown a capillary electrophoresis apparatus 10 having a cabinet 12, power supply 14, a sample injection system 16, a sensing section 18, a sample changing system 20, an electrophoresis section 22 and a fraction collector system 21. This capillary electrophoresis apparatus is similar to the apparatus 10 disclosed in United States application Ser. No. 277,566 filed Nov. 29, 1988, in the name of Robert William Allington and assigned to the same assignee as this application but includes a fraction collector section 21. The cabinet 12 is shown in FIG. 1 with its top removed. It supports the power supply 14, the sample changing system 20, the electrophoresis section 22, the sensing section 18, the sample injection system 16 and the fraction collector system 21 which are connected together to separate molecular species.

The electrophoresis section 22 is connected to the sample changing system 20 and adapted for maintaining at least one portion of the electrophoretic separating region of the capillary tube horizontal. The sensing section 18 is connected to the electrophoresis section 22 and includes a light absorbance detection cell for monitoring the separation, and an improved way of introducing a precise sample volume to be described hereinafter. The fraction collector section 21 includes a plurality of sample collection cells 412–448 housing 411, electrodes and a drive mechanism. The sample cups are adapted to received separated molecular species.

To remove the carrier 411 and deposit effluent in individual cells, the sample injection and fraction collection mechanism 21 includes carrier 411 and the controllable-pressure vessel with cap 98. The carrier 411 and controllable-pressure vessel are supported on a support plate 410 (FIG. 7) which moves slideably, horizontally on guide rails 406 and 407. The capillary tube 30 may be led through removable cap 98 (FIG. 14) which covers the controllable-pressure vessel 80 under the cap 98. The vessel is mounted in a recess in support plate 410 (FIG. 7) and moves with carrier 411.

Sealing piece 400A (FIG. 7) is in the shape of a frustum of a cone and makes a seal with conical hole 501 (FIG. 13) in cap 98 when arm is lowered. The vessel may have a vacuum applied to it through flexible connecting tubing 94 for initially filling the capillary tube with electrolyte and for loading sample into the capillary tube as disclosed in the preceding application. Connecting tubing 94 is lead through hole 502 in mounting surface 405 to the sample injection system pressure control system 16. The pressure control part of the sample injection system is located under mounting surface 405. When operating, the injection apparatus establishes a negative pressure in the vessel under cap 98 which pulls filling buffer into the capillary tube 30 from one of the buffer beakers 60A, 60B, 60C or 60D; or a small amount of sample from one of the sample vessels located on sample changer 20 in a manner similar to that disclosed in U.S. patent application Ser. No. 07/277566.

The carrier 411 holds a number of sample collection cups 412 through 448 (FIG. 13). Carrier 411 is equipped with a grounding electrode 505 (FIG. 7) which is immersed in conducting electrolyte 451. Electrode 505 is connected by flexible conductor 90 and is led through hole 503 in mounting surface 405 to the electrical ground connected to terminal 105 of the high voltage power supply 14 in FIG. 1. Carrier 411 also has electrode 555 which is immersed in to conductivity electrolyte 450.

With this arrangement, the sample changer section 20 causes one end of the capillary tube 30 to contact a sample and the sample injection system 16 pulls sample into the end, and causes one end of the capillary tube to be in contact with a buffer at a potential suitable for electrophoresis. Power is applied at a high potential while the sample is within the part of the capillary tube which is horizontal to rapidly electrophores the sample with low diffusion. The separated bands are sensed and collected by: (1) transmitting light through narrow slits on opposite sides of the separating medium in the sensor: (2) determining the absorbance of the bands; and (3) collecting the bands in sample cells that are moved into position to receive one or more or a part of one of the sensed bands in response to signals from the sensor bands.

In the preferred embodiment, the sample changing section 20 inserts one end of the capillary tube into a sample, and after the sample injection system section 16 has pulled sample into the end, the sample changing system 20 inserts the end of the capillary tube into a buffer from an electrolyte section 50. Power is applied and, when the sample is in a horizontal portion of the capillary tube, the voltage is increased to speed the separation.

In some embodiments, the capillary tube is horizontal throughout its length of electrophoresis and the sample changer need not move the end of the capillary tube from the sample to the buffer. In this embodiment, the horizontal capillary tube that contains sample is inserted horizontally into the buffer by means of some suitable method such as piercing a resealable container. In another embodiment, the sample containers and buffer are moved into contact with the end of the capillary tube rather than moving the end of the capillary tube.

The electrophoresis section 22 is located within the cabinet 12 for temperature control during electrophoresis and includes a capillary tube 30, a removable horizontal cover plate 32 and a horizontal ledge 34, which cover plate 32 rests on the horizontal ledge 34 in the cabinet 12. The removable horizontal cover plate 32 and horizontal ledge 34 contain the capillary tube 30 between them within a recess in the horizontal ledge 34 shaped to permit a change in the length of the capillary tube 30 between the removable horizontal cover plate 32 and horizontal ledge 34. This permits the movement of the end of the capillary tube 30 by a sample changer while the capillary tube 30 is maintained in a horizontal position even though the distance between the sample changer and the light sensor changes.

The capillary tube 30 has: (1) a first end that extends from the electrophoresis section into the sample changing system 20 where it is held for contact with the sample and buffer, which may be by movement into the sample and buffer solution; (2) a central section within the electrophoresis section which is preferably horizontal and through which electrophoresis takes place under some circumstances at high voltage; and (3) a second end section that extends from the electrophoresis section into the sensing section 18, the sample injection system 16 and the fraction collecting system 21.

The capillary tube 30 is made of quartz in the preferred embodiment with an inside diameter of between 0.03 and 0.2 millimeter and may include any separating medium. The capillary tube wall in the preferred embodiment is in the thickness range of between 0.1 and 0.2 millimeters. While a capillary tube of the conventional type for electrophoresis is contemplated for the preferred embodiment, other sizes of tubes and tubes of other materials may obviously be used.

To provide temperature control by cooling the horizontal section of capillary tube 30 within the elongated horizontal recess in ledge 34, the horizontal ledge 34 (FIG. 3) and removable horizontal cover plate 32 (shown in phantom in FIG. 3) are preferably made of highly thermally conductive material and/or the removable horizontal cover plate 32 includes extensive perforations to facilitate cooling of the capillary tube 30. The removable horizontal cover plate 32 may be removed with handle 36.

To permit the capillary tube 30 to extend beyond the elongated recess and the horizontal ledge 34 to the sample changing system 20 and the sensing section 18: (1) a notch 40 is provided at one side (the left end as viewed in FIG. 3) in horizontal ledge 34 to receive the capillary tube 30 from the sample changing system 20; and (2) another notch is provided in the other end, which is the right end as viewed in FIG. 3, to permit the capillary tube 30 to pass out of the electrophoresis section through hole 38 in the sensing section 18.

To supply samples to the capillary tube 30, the sample changing system 20 includes a sample holding reel 44, a movable arm 46, a rotor head 48 and an electrolyte section 50. The sample holding reel 44 and electrolyte section 50 contain sample and electrolyte in spaced apart containers. The movable arm 46 is carried by the rotor head 48 and is movable in two directions to insert an electrode in the electrolyte and the end of the capillary tube 30 into the electrolyte and sample.

This electrode 52 and the capillary tube 30 are mounted by a bracket 54 to the movable arm 46 of the sample changing system 20. The bracket 54 mounts the capillary tube 30 at a horizontal level that is, when the end capillary tube is lowered into contact with the electrolyte, the same as the level of the recess in the horizontal cover plate 34 and the level of the sensor 72 to maximize the length that is horizontal. In one embodiment, the arm moves up and down through slot 56 in rotor head 48 of the sample changing system 20.

In another embodiment, the arm and its shaft move up and down and rotate and the rotor casing is not necessary. This enables dipping the capillary tube 30 in sample vials indicated as 58A, 58B, (etc.) in the removable sample holding reel 44. The removable sample holding reel 44 is programmably rotatable to bring any of its 40 sample tubes under capillary tube 30 and rotor head 48 is rotatable to place the capillary tube 30 either over a sample tube or over electrolyte vessels 60A, 60B, 60C or 60D in the electrolyte section 50.

When the desired electrolyte vessel or a sample tube is selected by rotation of rotor head 48, movable arm 46 moves downward to put the end of capillary tube 30 either in contact with the sample in the sample tube or with the electrolyte 62A, 62B, 62C or 62D in an electrolyte vessel. When the end of the capillary tube 30 dips into the electrolyte in an electrolyte vessel, an electrode manifold 301 energizes an electrode 52 in the electrode in the vessel. Thus, the desired electrolyte vessel is energized by the electrode 52 and selected by the capillary tube 30.

The electrolyte section 50 (FIG. 1) includes a motionless but easily removable electrode manifold 301 that dips multiple platinum electrodes simultaneously into all of the electrolyte vessels rather than dipping both the electrode and the capillary into the electrolyte vessels as described above to establish a potential across the tube. This action establishes one potential on the capillary tube 30 for electrophoresis with the other electrical connection to be described hereinafter as a permanent connection in a buffer although the circuit may be broken and established at programmed times.

Figure 2:
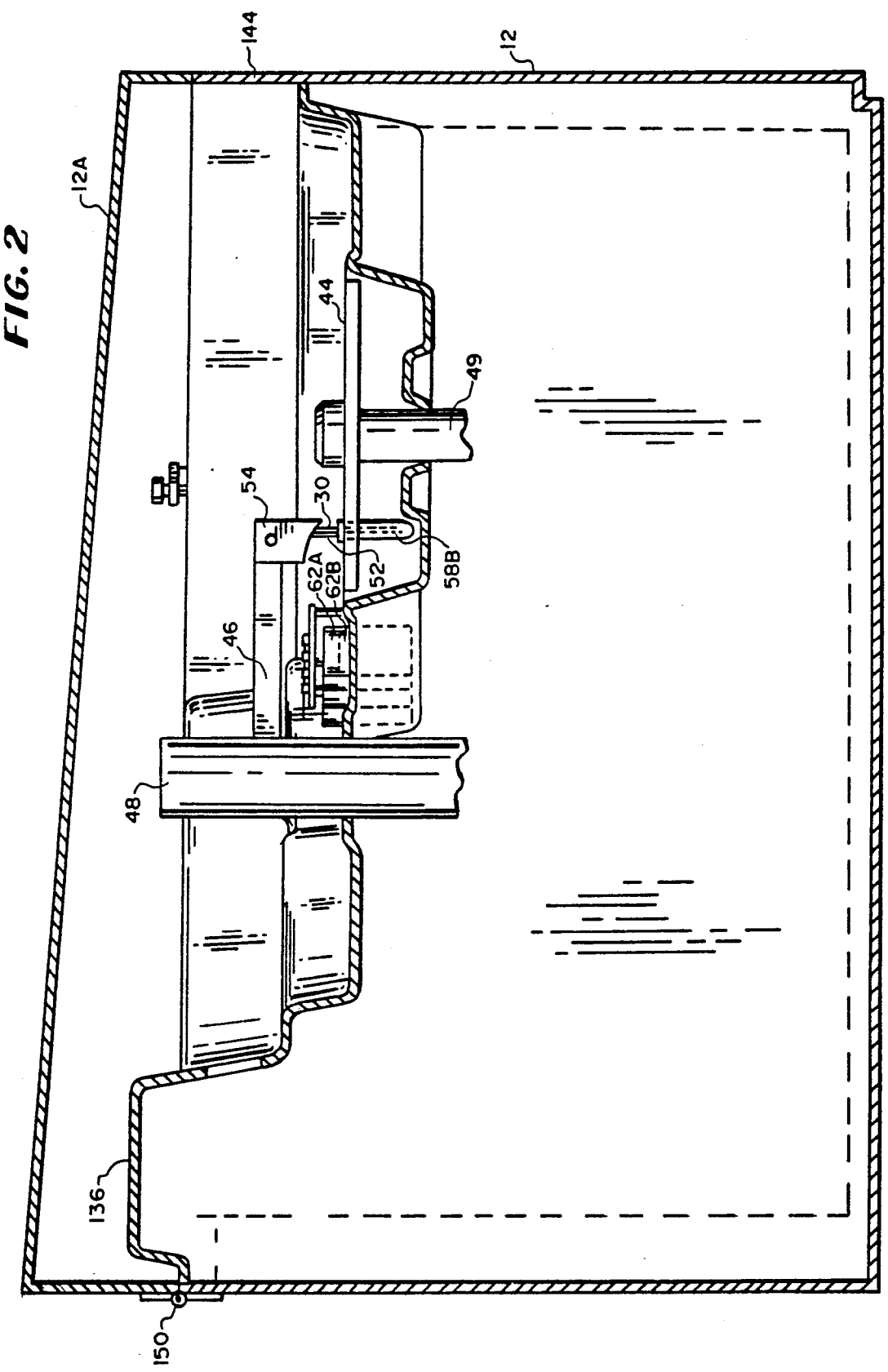
FIG. 2 is an irregular cross sectional view taken generally through a sample collecting mechanism of the apparatus shown in FIG. 1, looking from the left.

The electrode manifold 301 has four removable platinum wire electrodes 300A, 300B, 300C and 300D attached to it. These electrodes dip into four buffer electrolyte beakers 60A, 60B, 60C and 60D. Pivotally mounted grounding clapper 301A is released by an electromagnet (not shown in FIG. 1), located below the mounting surface 405 to act as a safety ground by swinging against the electrically conducting electrode manifold 301 when overhead access lid 145 in FIG. 2 is opened. Preferably, the grounding clapper 301A should incorporate a resistive path to ground and not a highly conductive path to ground so the high-energy sparks are not formed during the grounding process. High-energy sparks might disrupt nearby electronic circuitry.

The sensing section 18 (FIG. 1) includes an absorbance monitor 70 and a sensor 72 located inside sensor cassette 74. The absorbance monitor 70 and sensor 72 utilize the optics, circuitry and structure of the absorbance detector described in United States Pat. Nos. 4,726,680 and 4,523,097 for liquid chromatography absorbance detectors.

For capillary electrophoresis purposes, the detection volume, which limits the volume resolution of separated bands, is smaller than is usual for liquid chromatography absorbance detectors. The detection volume for capillary electrophoresis should be smaller than 100 nanoliters, and often is in the range of 1 to 10 nanoliters. This is because of the very small volume of separated bands. The detection volume is the volume containing separation medium through which light passes between the light source and active area of light sensor before being sensed.

The absorbance monitor 70 incorporates a light source for illuminating one side of sensor and a light detector for detecting light exiting the opposite side of sensor 72. It is substantially the same detector turned on its side so that the flow cell is on top and has a horizontal flow axis or plane, instead of being mounted on the side of the detector and having a vertical flow axis or plane. Of course, the flow cell and separating system are adapted for capillary electrophoresis as described herein, instead of for liquid chromatography as described in the foregoing patents.

To sense bands, the capillary tube 30 enters sensor 72 (FIG. 1) after passing through hole 38 in cassette 74 (FIG. 1). Sensor 72 may be equipped with fixed or adjustable slits to align a very narrow measuring light beam so that it goes exactly through the liquid filled part of the capillary tube 30. In some embodiments, the position of adjustable slits may be adjusted by screw adjustment 76 (FIG. 1) as described hereinafter but this is not necessary.

The sample injection system 16 includes a controllable pressure buffer and electrode vessel 80, an electrical interface 82, a low vacuum tank 84 and a pressure control solenoid valve 88 which is connected by connecting tubing 94 to electrode vessel 80. The buffer and electrode vessel 80 communicates with the common port 108 of solenoid valve 88. Pressure sensor 80A is connected through tube 94A to tube 94 to sense vacuum pressure in contact with the surface of the buffer during sample injection. Electrode vessel 80 also may provide an electrical connection to the capillary tube 30 during electrophoresis.

For these purposes, vessel 80 has a connection (not shown) to the ground terminal power supply 14 through conductor 90. Pressure sensor 80A has a connection to the electrical interface 82 to provide a measured pressure signal through a cable 92 and to the pressure control solenoid valve 88 through a pressure line or connecting tube 94. The pressure control solenoid valve 88 communicates with the vacuum tank 84 which is connected to the pump assembly 86. The electrical interface 82 may include an integrator to provide a signal proportional to the sample and may be performed in a computer connected to the electrical interface 82.

The capillary tube 30 extends into the fraction collector section 21 and is mounted to a movable lifting and rotating arm 460 of a fraction collector buffer container 411. The container 411 is partly filled with electrolyte buffer.

To establish an electrical connection through the capillary tube 30 for electrophoresis, the fraction collector 21 receives electrode (not shown) in vessel 80 and the capillary tube 30 and this electrode dips into electrolyte buffer. The electrical conductor 90 is connected to this electrode and to the ground terminal 105 of power supply 14. Connecting tubing 94 pierces cap 98 but does not dip into electrolyte buffer 100.

To draw a controlled amount of sample into the end of the capillary tube 30 with a measured pressure: (1) connecting tube 94, the electrode and the capillary tube 30 are sealed airtight into the removable cap 98; (2) the removable cap 98 is sealed air tightly to vessel 80; and (3) a pressure sensor 80A communicates to the interior of the electrode buffer vessel 96 through tubes 94A and 94 and senses the pressure therein. The electrical connection 92 connects the pressure sensor 80A to an electrical interface 82 which is connected by a lead 106 to a conventional controller or computer 119 not described in connection with FIG. 1. In the alternative, the signals may be recorded with conventional recording equipment and the operation of the sample injector and movable arm 46 may be manually performed.

To supply negative pressure to the vessel 80, the connecting tubing 94 communicates with the common port 108 of pressure control solenoid valve 88. Normally open port 110 of this valve is vented to the atmosphere and the normally closed connection 112 of this valve is onnected to tubing 114 which leads to low-vacuum tank 84 so that energization of the pressure control solenoid valve 88 applies vacuum pressure to the vessel 80.

To energize the pressure control solenoid valve 88, a conductor 116 is electrically connected to a controller or computer or a manually-operated electrical switch 117 connected to a source of power and supplies power to the solenoid of the pressure control solenoid valve 88. This controller or manually-operated electrical switch supplies signals to initiate the sample injection while the capillary is held in the sample well by the movable arm 46.

To maintain the vacuum pressure in the low-pressure vacuum tank 84, tubing 120 connects the low-pressure vacuum tank 84 to vacuum pump assembly 86. The vacuum pump assembly 86 includes a vacuum pump 122 mechanically connected to electric motor 124 through coupling 126. A vacuum sensor 128 turns on motor 124 through a signal on lead 130 when the pressure in the tank becomes too high. This establishes a controlled negative pressure in the tank 84. Preferably, the setting of the vacuum sensor is adjustable or programmable.

The high voltage power supply 14 is located inside the cabinet 12 and is fitted with ground terminal 105 and high voltage terminal 132. The power supply 14 is preferably capable of supplying a regulated voltage from 1,000 to 40,000 volts at a current of up to 400 microamperes. A high voltage insulated cable 134 is connected to high voltage terminal 132 and terminates (connection not shown) in platinum wire electrode 52 and electrode manifold 301.

A conventional air cooling and temperature control unit (not shown) are housed in cabinet 12. A fan incorporated in this unit blows temperature conditioned air out through vent slots 140 located in venting unit 136. Return air to the air conditioning mechanism is through vent slots 138. This air conditioning feature ensures that the electrophoresis process operates at a repeatable temperature that does not vary significantly over a period of time. The air enters and flows above the sensor 72 blows through heat transfer fins 76A, which are thermally connected to cassette 74 and sensor 72, and then is routed past the capillary tube between its sample inlet end and the sensor 72 by conventional baffling not shown in the figure. Temperature control of electrophoretic separations is a common feature of electrophoresis apparatus.

The air supply vents 140 are thermally coupled to the sensor 72 under sensor mounting plate 302 in FIG. 1 herein. The sensor is temperature controlled by the air exiting the vents 140 as its passes through fins 76A mounted on cassette 74. The cassette and the sensor located directly beneath it are removably fastened to the absorbance detector by captivated by loosenable mounting screws (not shown).

In FIG. 2, there is shown a sectional view of the cabinet 12 taken through lines 2—2 of FIG. 1 and showing the rotor head 48, movable arm 46, capillary tube 30, sample vials such as 58B and a lid 145. As shown in this view, the cabinet 12 is: (1) insulated; (2) includes a top surface 12A that slopes upward from front to back; and (3) is fitted with a lid 144 (FIG. 2) which preferentially has metal sides and a transparent top. The lid 144 is hinged to the cabinet 12 with hinge or hinges 150. The cabinet 12 preferentially has an outer metal surface which, along with the sides of the lid 144, are electrically grounded for safety. As shown in this view, the bracket 54 mounts the capillary tube 30 at a location adjacent to the electrode 52 so that the capillary tube 30 is insertable into the sample vial 58B and the electrode 52 may be moved to the buffer vessel 62A for insertion in the buffer 60A by rotating the arm 46.

When a new sample is desired, a rotor 49 rotates the table 44 to move a new sample in position under the arm and the arm is swingable between the buffer vessel 62A and the sample housing reel 44. As it rotates, the capillary tube 30 extends through the notch 40 in the removable horizontal ledge 32 (FIG. 3) where it is inserted into coils therein which expand or contract to take more or less tubing as the arm 46 moves. With this arrangement, the capillary tube 30 remains horizontal between its connection with the bracket 54, the recess in the horizontal ledge 32 (FIG. 1) and the sensor 72 (FIG. 1).

Figure 3:
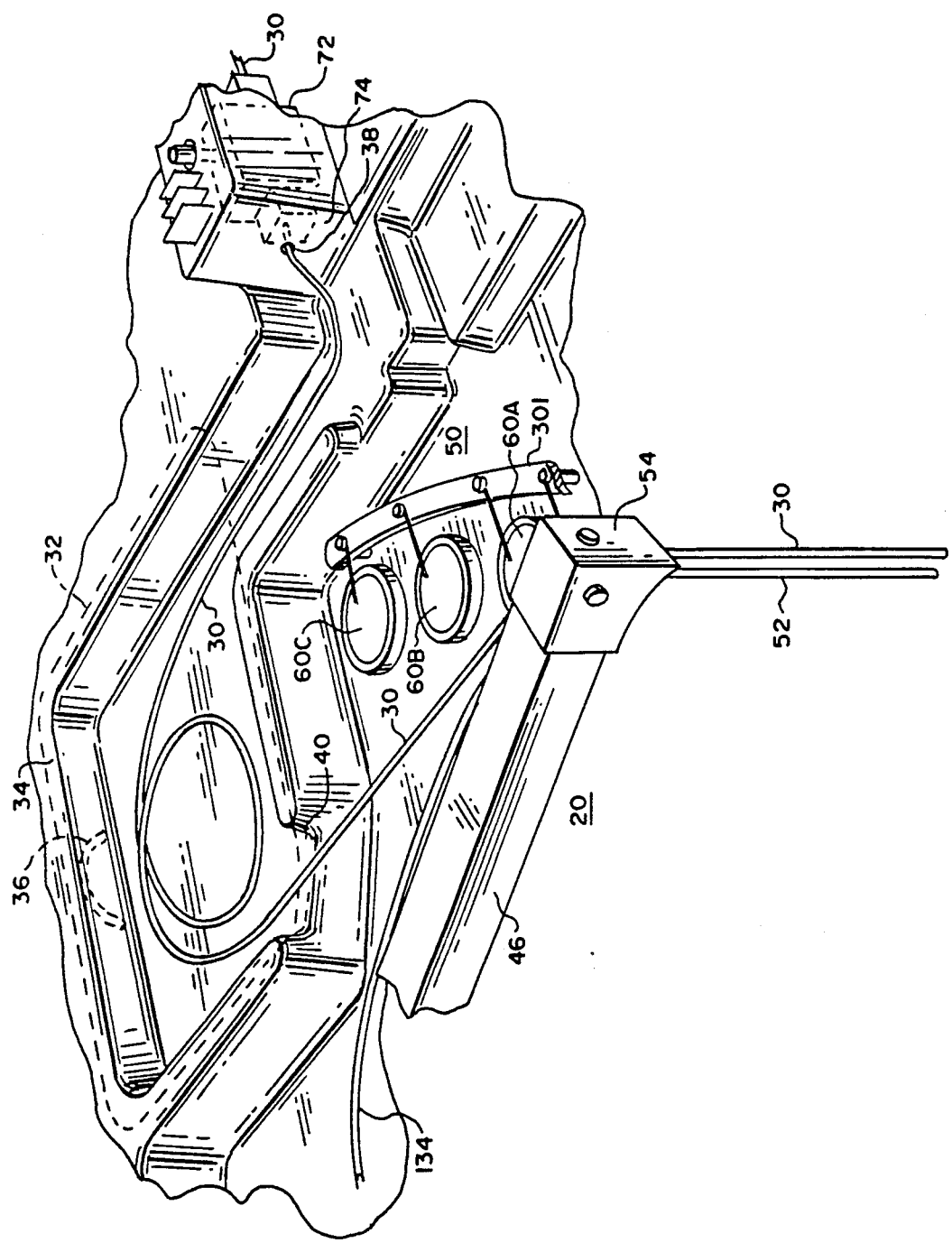
FIG. 3 is a simplified fragmentary perspective view of a portion of the apparatus of FIG. 2.

In FIG. 3, there is shown a simplified fragmentary view of a movable arm 46, a flexible electrical conductor 134 for high voltage, a capillary tube 30, and a sensor 72 with the capillary tube 30 being positioned in a recess in the ledge 34 (the cover plate 32 is removed in this view). The bracket 54 is shown having an opening adapted to mount one end of the capillary tube 30 for movement from sample to buffer. As best shown in this view, the horizontal ledge 34 includes a recess in which the capillary tube 30 is coiled so that it may receive more or less tubing as the movable arm 46 swings between a buffer location and a sample location. The bracket 54 supporting the capillary tube 30, the recess in the surface 34 and the fitting for the sensor 72 are all in the same horizontal plane so that, as the electrophoresis apparatus is operated, the capillary remains horizontal.

Typically, the inside diameter of the tube is 50 to 75 micrometers and the outside diameter is 375 micrometers. The length of the interior of the tube is filled with a liquid buffer electrolyte. An electric field is established along the axis of the tube by conventional means and electric current flows through the tube.

Figure 4:
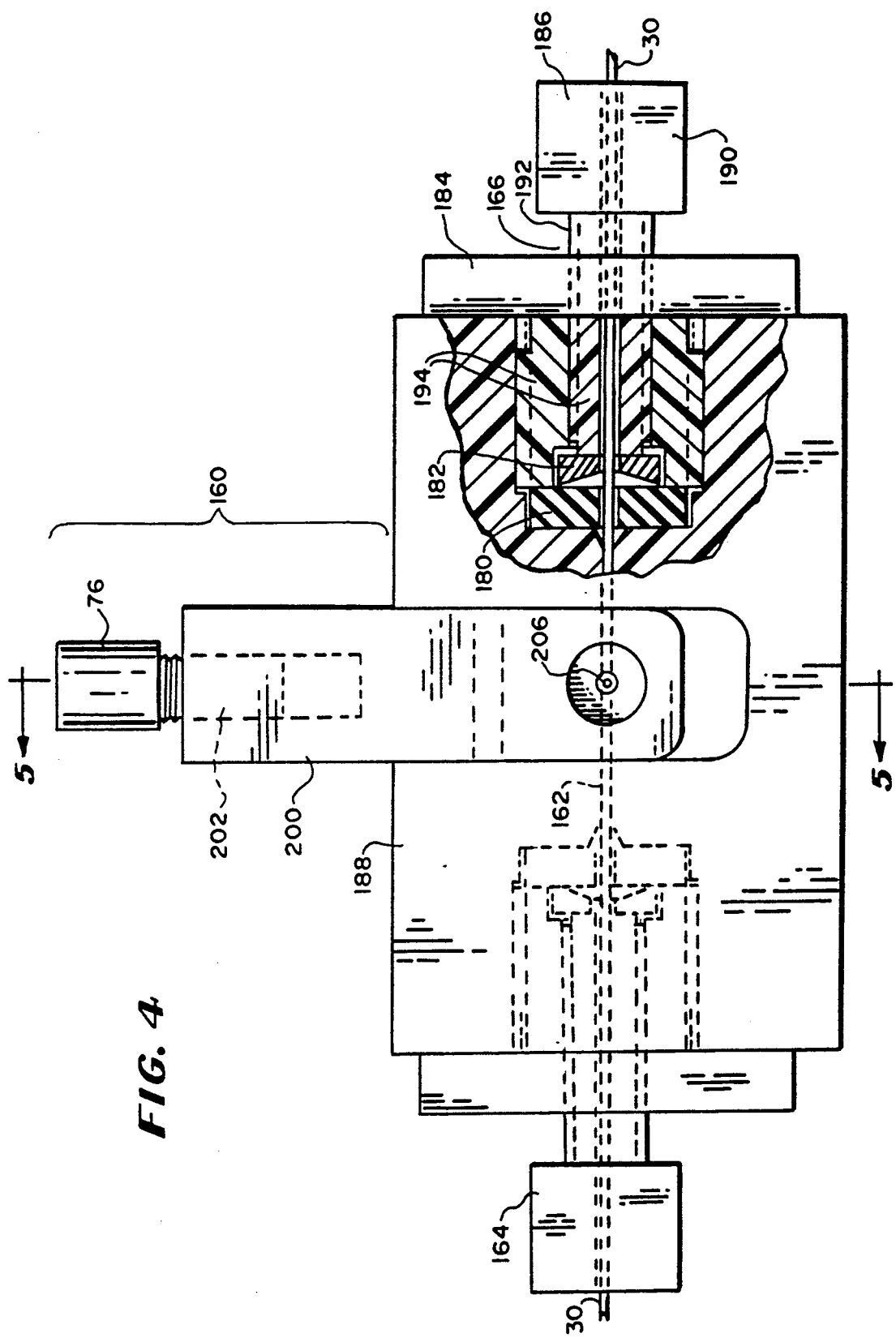
FIG. 4 is a side elevational view, partly broken away and sectioned, of a flow cell useful in an embodiment of the invention.
Figure 5:
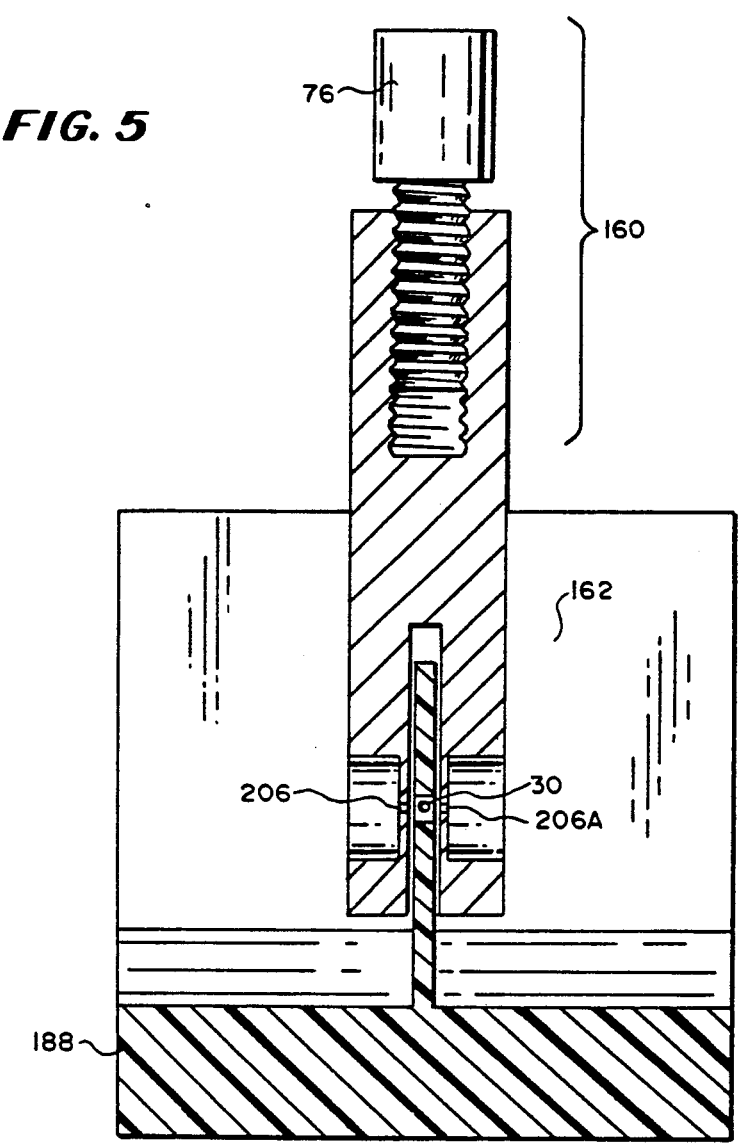
FIG. 5 is a sectional view taken through lines 5—5 of FIG. 4.

In FIG. 4, there is shown a side view partly broken out and sectioned showing the sensor 72 having an adjustment section 160, an optical slit section 162, a first fitting assembly 164 for the capillary tube 30, and a second fitting assembly 166 for the capillary tube 30.

The capillary tube 30 is received in the first and second fittings 164 and 166, which cause the capillary tube 30 to extend along the axis of the sensor 72 and between the slits in the optical slit section 162. The location of the two slits in a direction perpendicular to the axis of the capillary tube 30 is adjusted by the adjustment section 160.

The sensor 72 is attached to a cassette or mounting plate for mounting in the absorbance monitor 70 (FIG. 1) and receives the capillary tube 30. To mount the capillary tube 30, the two fitting assemblies 164 and 166 are adjustable. They are identical in structure and only the fitting assembly 166 will be described in detail herein.

The fitting assembly 166 includes a rubber washer 180, a stainless steel squeezer 182, a plastic threaded closure 184 and a plastic threaded fastener 186. The threaded fastener 186 is positioned to be tightened to hold the threaded closure 184 in place where it supports a threaded sleeve. The threaded fastener 186 also presses the stainless squeezer 182 against the rubber washer 180 to provide a seal around the capillary tube 30.

In this embodiment, the housing 188 of the sensor 72, the threaded fastener 186 and the threaded closure 184 are all formed of a relatively hard plastic such Delrin (trademark of the DuPont Corporation). The washer 180 is a flexible, elastomeric material which may be the thermoplastic rubber Kraton. A central aperture extends through the washer 180, the stainless steel squeezer 182, the threaded closure 184 and the fastener 186 to accommodate the capillary tube 30 which extends along the longitudinal axis, past the optical slit section 162 where the optical sensing is performed and through the fitting assembly 164 on the opposite side of the sensor 72.

To force the washer 180 around the capillary tube 30, the washer 180 is generally cylindrical with a cylindrical central opening receiving the capillary tube 30. It fits conformably in a counterbore within the housing 188 of the sensor. The stainless steel squeezer 182 is generally cylindrical but has an inwardly tapering cone positioned adjacent to the washer 180 and a central aperture to accommodate the capillary tube 30 so that when it is pressed inwardly, it forces the washer inwardly towards its central opening and outwardly against the counterbore.

To force the stainless steel squeezer 182 against the washer 180, the threaded fastener 186 includes a thumb handle 190 and a threaded shank 192, with the threaded shank 192 extending downwardly through the plastic threaded closure 184 where it engages a correspondingly threaded metal sleeve 194 threaded into a tapped hole of the Delrin housing. The threads within the tapped hole are within a metal sleeve molded within the aperture of the Delrin housing so as to remain fixed in position and still accommodate threads. The mechanism of the fittings are designed to accommodate the capillary tube 30 in such a way that the capillary tube 30 is held immobile in the light sensor 72.

The adjustment section 160 includes an adjustment screw 76 fixedly mounted (by convential means not shown in the figure) with respect to the housing 188 and an optical slit carriage 200. The optical slit carriage 200 is stainless steel and threaded at 202 in its upper portion with internal threads complementary to the external threads on a shank of the tightening screw 76 so that as the adjustment screw 76 is rotated, the carriage is moved up and down with respect to the housing 188 of the sensor 72. The optical slit section 162 is mounted to the bottom of the optical slit carriage 200 to be raised and lowered therewith and includes on each side a relatively short optical slit 206 having a longitudinal axis aligned with the longitudinal axis of the capillary tube 30. There are two such slits which closely straddle the capillary tube 30 (FIG. 9) a cross section through line 9—9 of FIG. 8, more clearly shown the relationship of the two slits 206 and 206A to the capillary tube 30. FIG. 9 shows the narrow dimension of the slits, which is 100 micrometers in the preferred embodiment. Preferably, the distance between the slits is between one and three times the outside diameter of the capillary tube.

More specifically, the rubber washer 180 is compressed around the capillary tube 30 to hold the tube in place. The rubber washer 180 preferably is made of white, food grade, Kraton (trademark) thermoplastic rubber which does not deposit any ultraviolet light absorbing materials on the quartz tube as the rube is pushed through the washer. Kraton is available from Shell Corporation. The rubber is compressed radially to tighten around the tube by pushing the female cone-shaped stainless steel squeezer 182 against it by turning a plastic threaded fastener 186. The threaded fastener 186, stainless steel squeezer 182 and washer 180 are captivated within the housing 188 of the light sensor 72 by the threaded closure 184 which screws into a threaded recess in the housing 188. The tightener, captivator and housing are advantageously made out of Delrin (trademark of DuPont) plastic.

Figure 6:
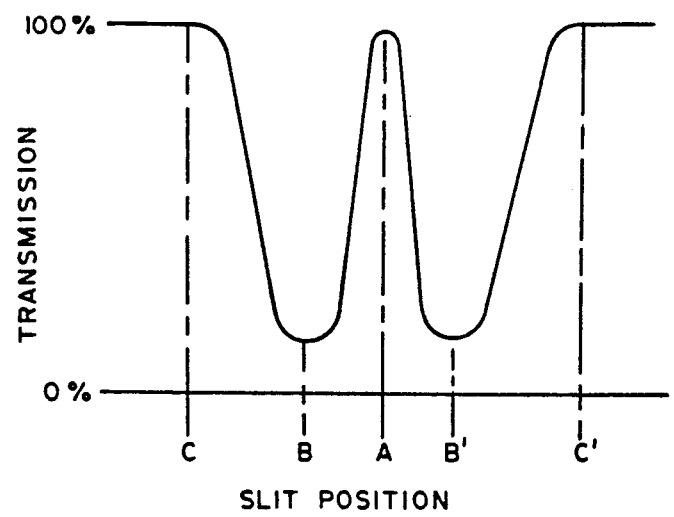
FIG. 6 is a graph containing a curve representing transmission with different positions of slits related to the embodiments of FIGS. 4 and 5.

In one embodiment, the optical slit carriage 200 is moved with the adjustment screw 76 to center a pair of optical slits, one of which is shown at 206, each being 0.01 inch (250 micrometers) long by 0.004 inch (100 micrometers) wide, over the capillary tube 30 extending through the light sensor. However, the slits may be fixed in position. The dual slits are exactly corresponding elements mounted exactly opposite each other across a bifurcation of the optical slit carriage (FIG. 6). The capillary tube 30 lies within the bifurcation. The long direction of the slit is parallel to the axis of the capillary tube 30. When the adjustment screw 76 is turned in the adjustable slit embodiment, the optical slit 206 moves transversely with respect to the capillary tube 30. The capillary tube 30 is firmly held within the bifurcation by two holders.

Figure 10:
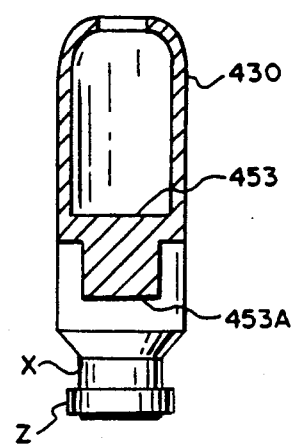
FIG. 10 is a cross section taken through 10—10 of FIG. 9.

The sensor 18 is inserted in the absorbance monitor 70 located within the cabinet 12 in FIG. 1. In FIG. 1, the sensor is generally shown at 18. The capillary tube 30 is filled with water or buffer. Light from the light source of the absorbance monitor enters one of the pair of slits in the sensor 18, and when the sensor 18 is properly adjusted, light exits the other slit and impinges upon the light detector of the absorbance monitor. To make this adjustment, the adjustment screw (shown as 76 in FIG. 4, is rotated and the indication of the absorbance monitor 70 is monitored. Starting at one extreme of rotation on the tightening screw 76, and referring to FIG. 10, the following is observed.

At slit position C, the slit is entirely beyond the capillary tube 30 and light travels through the free space between the pair of slits. As the adjustment screw 76 is rotated, the light beam cuts through the curved edge of the capillary tube 30 which deflects most of the light going through the first slit so it does not go through the second slit. At slit position B, almost all of the light is lost, and a minimum of light transmission is indicated on the absorbance monitor.

Assuming that the capillary tube 30 is properly filled with water or electrolyte buffer (no air in the tube at the light path), continued rotation of the adjustment screw so that the pair of slits are centered on the tube greatly increases the transmission again, to a well defined maximum at proper alignment. This is shown as slit position A in FIG. 6.

Further rotation of the adjustment screw 76 produces transmission indications as shown when moving from A to B' and then from B' to C' because of symmetry in the transverse direction. The absorbance monitor should be operated with the adjustment screw 76 set to slit position A, as determined from the local maximum transmission reading of the absorbance monitor itself.

Although the foregoing describes a flow cell with adjustable slits, there is no intention to argue that this arrangement is necessarily superior to a flow cell having a fixed aperture. The description is included only to provide information about one of a number of flow cell arrangements suitable for capillary electrophoresis.

Figure 7:
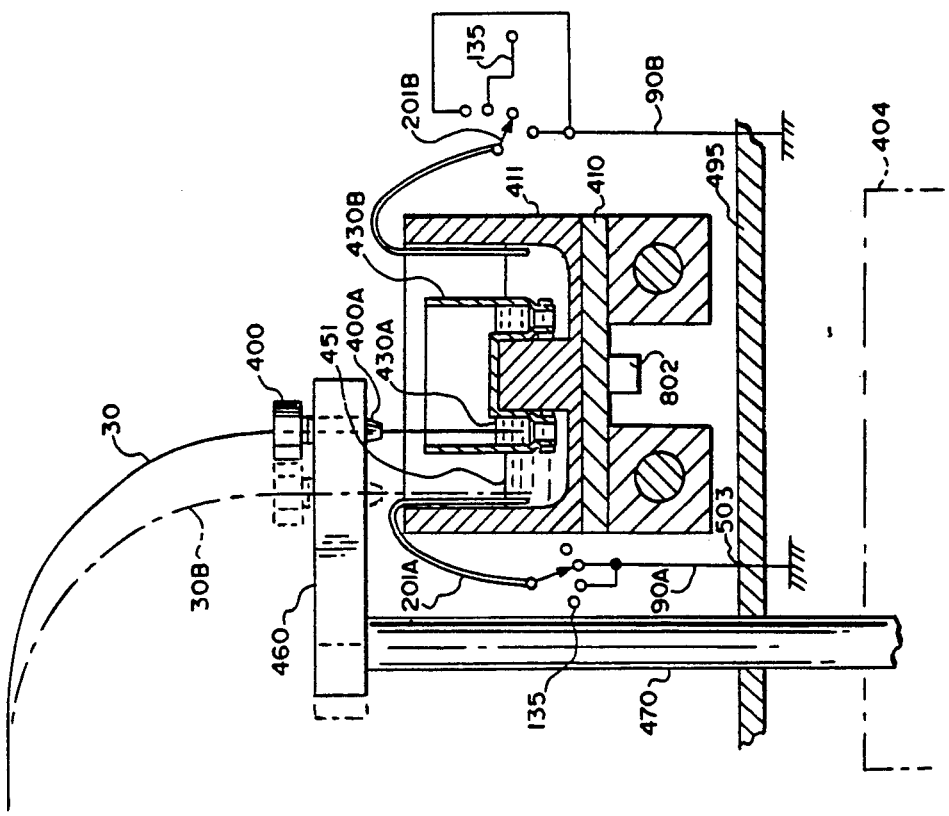
FIG. 7 is a cross sectional view of the fraction collecting mechanism of FIG. 1 indicating part of its operating cycle.

In FIG. 7, there is shown a fragmentary elevational view, partly sectioned and broken away, of the lifting and rotating arm 460, the carrier 411, and a sample collection cup 430. The lifting and rotating arm 460 has one end of the capillary tube 30 mounted through it for carrying upwardly and downwardly to move it into position for electrophoresis and sample collection and into another position for participation in the sample injection procedure.

The sample cups such as the cup 430 are adapted to be moved by the carrier 411 one at a time into a location where the capillary tube will be inserted into the buffer in the cup well 430A which communicates through semipermeable membrane 430B to the buffer 451 in the carrier to permit electrophoresis of samples into individual cells such as 430 for concentration in a manner to be described hereinafter against a membrane located near their bottom within the buffer in well 430A.

The sample cups are similar in construction to the sample cup 80 in FIG. 13 of U.S. Pat. No. 4,164,464, the disclosure of which is incorporated herein by reference. The fraction collector 21 includes a means 802 by which the plate 410 and carrier 411 may be moved and first and second electrical switches 201A and 201B which may be used to electrically connect either side of the dividing wall 452 of the carrier 411 to either ground or to disconnect the sides. Instead of a ground connection through conductor 90A or 90B, a low voltage (with respect to ground) supply 135 may be used.

With this arrangement, migration in either direction may be accommodated within the cells and the carrier 411 may be removed from its interlocking position in the plate 410 for sample concentrating or may remain within the capillary electrophoresis apparatus 10 during concentration of the sample within the cells. The direction of migration is controlled by selecting the proper potential to move the more dilute molecular species across the bridge 453 to the other compartment for concentrating against the membrane at the bottom of the compartment. To concentrate the sample, the buffer liquids are generally raised above the bridge 453 a slight amount.

To align and move the carrier 411, sample cup by sample cup, during use, a rack 802 extends below support blocks 405 and 409 and between them for engagement with a pinion (not shown in FIG. 7). This permits the movement of the support blocks 405 and 409, the support plate 410, the carrier 411 and the vessel (not shown in FIG. 7) mounted within the support plate 410 along parallel guide rails 406 and 407 which are engaged by the support blocks 405 and 409. The support blocks 405 and 409 are fastened to the support plate 410 which, removably engages the carrier 411 (not shown).

The vessel 80 is mounted in a recess in support plate 410 (FIG. 7) and moves with the carrier 411. To connect the capillary tube 30 to the cap 98 and the vessel 80, the latter are slid into position under the capillary tube. Capillary tube 30 is sealably guided into cap 98 by threaded, tightenable, bushing 400, cap sealing pierce 400A, and tube fixing elastic washer 400B (FIG. 7). Bushing 400 is screwed into lifting and rotating arm 460. Screwing in bushing 400 compresses washer 400B against sealing piece 400A, forcing the washer to hold capillary tube 30. The lifing and rotating arm 460 is supported by lifting and rotating rod 470. Lifting and rotating rod is lifted and rotated by lifting and rotating mechanism 404, shown in phantom.

To collect fractions, the sample cup 430 has two cells containing electrolyte, indicated as 430A and 430B. The bottoms of the wells are covered with clamped-on semipermeable membrane assemblies 430D and 430C respectively to permit the flow of buffer ions but not the migration of separated sample. Electrical continuity for the electrophoretic migration taking place in capillary tube 30 is provided through the electrolyte in well 430A, the assembled semipermeable membrane 430D, electrolyte buffer 451 residing the carrier 411, the electrode 505 and the conductor 90 leading to electrical ground.

Separated zones are electrophoretically eluted or electrosmotically discharged from the capillary tube 30 into the electrolyte in well 430A, where they are trapped by the semipermeable membrane in assembly 430D. Each sample cup such as 430 has a connecting bridge 453 which provides fluid and electric connection between wells 430A and 430B if the electrolyte level is higher than that shown in FIG. 7. The bridge 453 is supported by supporting wall 452 which is a part of carrier 411.

To keep the separated samples in well 430A and prevent them from being transported to well 430B, either: (1) the level of the electrolyte or buffer in the wells 430A and 430B is lower than the height of the top of the bridge 453; or (2) the electrolyte or buffer level 450 and 451 in the two sides of the carrier 411 are lower than the height of the top of the supporting wall 452. Because of the possiblity of capillary forces drawing electrolyte within the carrier 411 over the space between the support 452 and the bridge 453, the electrolytes in the wells 430A and 430B preferably are lower than the height of the bridge 453 during this type of fraction collection.

The carrier 411 is supported by support plate 410, which in turn is supported by bearing blocks 408 and 409 which ride on support rods 406 and 407. This permits the carrier to slide in the direction perpendicular to the plane of FIG. 7 after the capillary tube 30 is withdrawn from the sample cup. The lifting and rotating mechanism 404 lifts arm 460 to effect this withdrawal. The position of the capillary tube, arm, bushing and lifting rod are shown in phantom (FIG. 7) as 30A, 460A, 400A and 470A respectively. In the phantom position the capillary tube is lifted above the top of carrier 411 and a conventional indexing mechanism (not shown in FIG. 7) moves the support plate 410, bringing the next sample collection cup into position for fraction collection, or the conical hole 501 (FIG. 13) in the removable cap 98 into position under the capillary tube 30 for injection of the next sample.

Figure 8:
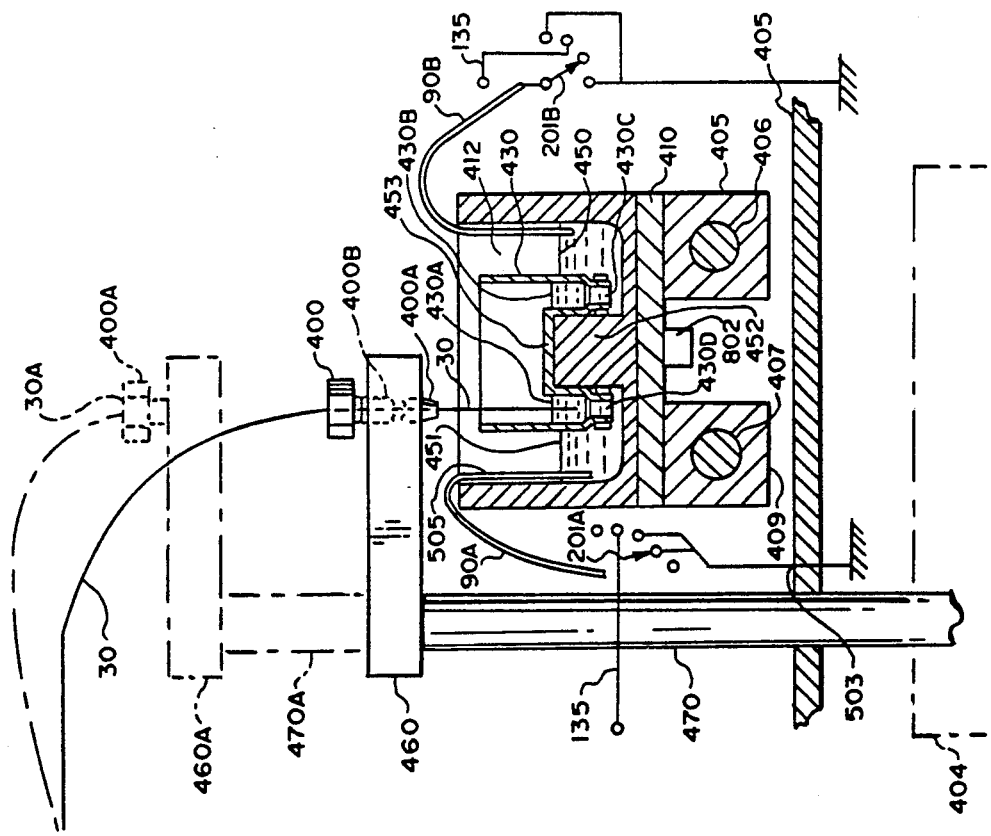
FIG. 8 is a cross section taken through the same plane as FIG. 7, showing another part of the operating cycle of the fraction collector.
Figure 9:
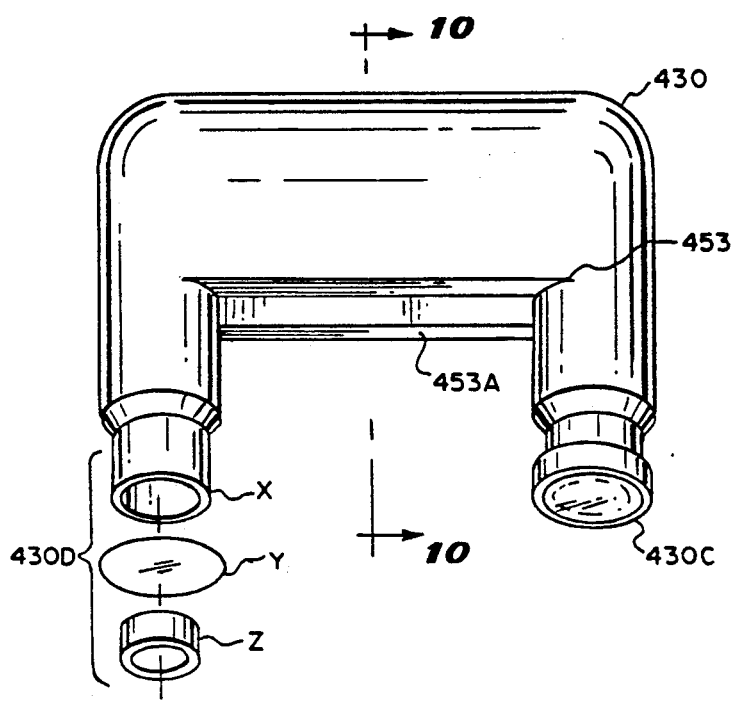
FIG. 9 is a perspective view of a sample collecting and concentrating cup, incorporating a trap, used in the fraction collector of FIGS. 1, 7 and 8.

In FIG. 8, there are shown two further positions of the capillary tube 30, the arm 460 and rod 470 of the lifting and rotating mechanism 404. The two positions are the collecting position (drawn solidly) and 30B at the waste position (drawn in phantom), corresponding to the two different rotational positions of arm 460 and rod 470.

To move from the collecting position to the waste position in FIG. 8, the arm 460 first is lifted by the rotating and lifting mechanism 404 to the position shown in phantom in FIG. 7. The waste (phantom) position of the capillary tube (30B) in FIG. 8 is used when no material of preparative interest is coming out of the capillary tube. Such waste material is discharged into the buffer 451 residing in carrier 411; and may be discarded later. The phantom position in FIG. 8 also corresponds to the sample injection postion for the arm 460 and capillary tube 30 shown in FIG. 1. The arm can also rotate to place the capillary tube 30 in electrolyte residing in well 430B in the other side of the cups 430.

In FIG. 9, there is shown an exploded perspective view of one sample collecting cup 430. The exploded view shown at 430D indicates how a semipermeable membrane may be assembled to the sample cup. As shown in this view, the sample cup includes a tubular cylinder X extending downwardly and forming walls of the well, a semipermeable membrane Y of diameter somewhat larger than that of the outside diameter of cylinder X, closing the well and an elastic band or ring of inside diameter somewhat smaller than the outside diameter of cylinder X. The semipermeable membrane Y is laid over the tubulation X and the elastic band Z is forced over to seal it in place. The complete assembly is shown at 430C.

The sample cup 430 has a key 453A molded into it, under the lower surface of bridge 453. This may be seen more clearly in FIG. 10 which is a sectional view taken through plane 10—10 in FIG. 9. Key 453A fits into one of the several slots 601A, 602A, 603A etc. in dividing wall 452 as shown in FIGS. 11 and 12.

Figure 11:
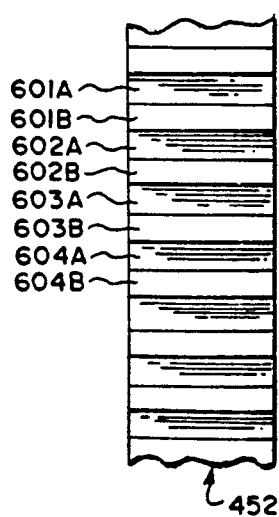
FIG. 11 is a top view of supporting wall forming a part of the fraction collector of FIGS. 1 and 7—10.
Figure 12:
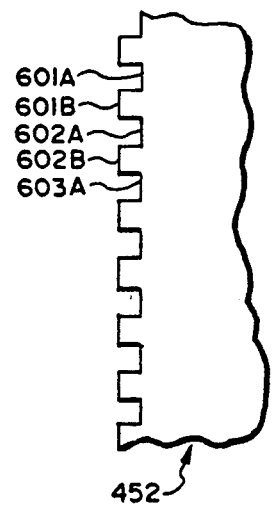
FIG. 12 is a side view of supporting wall of FIG. 11.

FIG. 11 is a top view of the supporting wall 452 of carrier 411. FIG. 12 is a broken-out section of the side view of the same wall. The keys 453A and aforementioned slots are sized and spaced such that sample cups 412 through 448 (FIG. 1) are located close together and accurately positioned within carrier 411. This is necessary so that the indexing mechanism (not shown in FIG. 9) that moves carrier 411 along guide rods 406 and 407 can accurately position the sample cups under the capillary tube 30. Alternatively, the sample cups may be fastened together rather than loose from each other, and only one locating or keying feature used for each group of fastened-together sample cups.

For fraction collection, operation starts in an initial cup 412 and proceeds in any one of several fraction collection patterns known in the art until collection is complete. FIGS. 14 and 15 may be used to explain a particular fraction collection cycle for one collecting tube. Reference is also again made to FIGS. 7 and 8.

Assume observation starts just before sample is to be collected in cup 430. Initially the arm 460 is positioned as shown at 460A in FIG. 7 with the capillary tube 30 above the well 430A in sample cup 430. The high voltage has already been turned off by a conventional programmer which is not shown. Lifting and turning mechanism 404 lowers the arm into the position indicated as 460 in FIG. 7. This lowers the capillary tube 30 into the electrolyte in well 430A of sample cup 430. This is called the "collection" position. After the capillary tube has been lowered into the electrolyte in well 430A and electrical continuity has been established, the programmer turns the high voltage power supply on and electrophoresed and or electro-osmosed material leaves the capillary tube 30 into the electrolyte in the collecting well 430A. This material from the capillary tube contains the sample component of interest. Solute in this material is trapped in the well, as it cannot pass through the semipermeable membrane at the bottom of the well.

When the sample component of interest has been completely eluted into the well, the programmer turns the power supply off. Then the lifting and rotating mechanism 404 raises the arm 460 to the position shown as 460A in FIG. 7. Next, the lifting and rotating mechanism 404 rotates the support rod 470, rotating the arm 460 to the position shown in FIG. 14. The lifting and rotating mechanism 404 then lowers the arm 460, putting it into the position shown in phantom in FIG. 8, with the capillary tube being in position 30B where it dips into the electrolyte 451 within carrier 411. This is called the "waste" position, and electrical continuity is re-established there. The programmer then turns the high voltage on and waste material between collected sample zones is eluted into the electrolyte 451 which later may be discarded.

When the next zone or peak of desired sample to be collected is about to be eluted, the programmer turns the power supply off and then lifts arm 460, the indexing mechanism (not shown in FIG. 7) advances the carrier 411 by rotating a pinion against a rack 802 one sample cup width towards the top of FIG. 14, the arm 460 is rotated so that it is in the position perpendicular to the carrier 411 such as in FIG. 13 and the arm 460 holding the capillary tube is re-lowered, this time into the next sample collecting cup 431. Then the programmer turns the high voltage on again.

This pattern repeats continuously. It is not limited to continuously going from one sample cup to the next, higher numbered, cup however. For example, with preparative work it may be desirable to make ten repeated, identical separations from a first sample located in sample changer 20 (FIG. 1) and collect say, three, sample components or fractions from each separation; and then go back to the same sample and do the same.

In a case like this, where there are three sample fractions to be collected from one sample in ten completely identical separation processes, it is advantageous to collect the first separation in the first, second and third cups, then back up the carrier and sample cups to the first cup again, and collect the second of the ten identical separations in the same three cups and repeat this process for ten times thereby saving on the use of cups and improving the yield due to less cup surface area that the sample might adsorb upon. Next, the three components of the second sample located in sample changer 20 would be collected ten times in the fourth through sixth cups, and so forth.

An important advantage of using sample cups such as cup 430 is that they can be used for concentrating the separated sample component after the elctrophoretic separation. This is done in a way similar to that described in U.S. Pat. No. 4,164,464. Generally, the sample cups such as 430 are stacked side-by-side in a carrier 411 which has been removed from the electrophoresis apparatus and then the samples are concentrated in the carrier by applying a potential across the buffer as explained more following in the aforementioned patents and the description hereinafter.

In FIG. 15, there is shown a cross sectional view of a cup 430, in a carrier 411 having more electrolyte buffer added to the cup so that the electrolyte covers bridge 453 as shown at 430E. Electrodes 505 and 555 are laid in electrolyte solutions 451 and 450 within carrier 411 and extend almost the full length within carrier 411. Electrolytic solutions 451 and 450 are mechanically and electrically separated by dividing wall 452. A potential difference of 100 to 200 volts is appplied to electrodes 505 and 555 as shown at B5 and differentiated by the symbols "−" and "+". Positively charged sample molecules in well 430A then migrate downwards and are trapped above the top surface of the semipermeable membrane shown at 430D.

After sufficient time has elapsed for concentration to take place, the sample cups are removed and placed vertically with the semipermeable membranes laying upon a firm surface. The concentrated sample lying just above the membrane may be pipetted off for further use at this time. In case the sample adheres to the membrane, the voltage on the electrodes 505 and 555 may be momentarily reversed to migrate the sample off the membrane or the membrane may be removed as indicated in FIG. 9.

Alternatively, concentration may be effected by using switch 201A–201B which is shown in FIGS. 7 and 8. It may be used to introduce the 100 to 200 volt potential difference electolyte solutions 451 and 452. This allows concentration without removal of carrier 411 from the electrophoresis apparatus in FIG. 1. It also allows filling the cup 430 with buffer above the level of bridge 453 before electrophoresis takes place.

The polarity of the electrode voltages in FIG. 15 is that which would be selected for positively charged sample molecules. If the sample is negatively charged, the polarity of the electrodes 505 and 555 may be reversed from that shown in FIG. 15. Alternatively, the electrode potentials may be kept the way they are as shown in the figure and the sample cup turned around so that the sample collecting well 430A is in contact with the electrolyte 450 adjacent to the positive electrode if concentrating time is not a factor. Thus, the positioned orientations shown in FIG. 15 may be maintained, and negatively sample charged being concentrated from well 430A will move across the bridge through the bridge electrolyte 430E and be concentrated in well 430B which now will be reversed to the position 430A on FIG. 15.

If the sample component being collected is composed of relatively large molecules, of moelcular weight over about 3000 daltons, the semipermeable membrane may be of fine-pored, relatively uncharged membrane such as fine-pored cellophane. Proteins are an example of such large molecules which will be trapped by fine-pored cellophane. If the sample components being collected are composed of molecules so small they can pass through the finest-pored cellophane, a specific ion-transmitting membrane can be used instead at 430D and 430C (FIG. 7) to trap the sample components. An example is Nafion (trademark of E. I. DuPont de Nemours) which preferentially passes only cations (positively charged ions).

In this example, buffer electrolyte cations in buffers 451 and 450 in the carrier 411 can pass through the specific ion membranes. During fraction collection, since membrane preferentially passes only cations, anionic (negatively charged) analate species will not pass through the membrane and will be trapped in the well 430A. For post-collection concentration (FIG. 15), the polarities of the potentials applied to electrode 505 and 555 are reversed from that shown in this figure.

Buffer cations in positive potential electrolyte solution 451 pass through the membrane at 430D, up well 430A, above bridge 430G, down well 430B, through the membrane at 430C and into negative potential electrolyte 450. Buffer anions cannot pass through either membrane. The flux of buffer cations within the cup 430 sets up an electric field that attracts the anionic analate within the cup towards the specific ion membrane at 430D. Analate molecules cannot pass through this specific ion membrane since they have the wrong charge to do so, and will concentrate above the membrane.

If the separated sample molecules (analate species) are cationic (positively charged), the membranes used at 430C and 430D may be anion-passing specific ion membranes. These will pass buffer anions to maintain electrical continuity during fraction collection and concentration, but trap the cationic analate. Of course, both the electrophoresing high voltage and the concentrating low voltage are reversed for separating carionic instead of anionic analate. The electrode polarities shown in FIG. 15 are proper for concentrating cationic analate. The high voltage electrophoresis voltage applied to vessels 60A, 60B, 60C or 60D (FIG. 1) should be negative for anionic analate and positive for anionic analate if electroosmotic flow in the capillary is not an oppositely-dominating factor.

Some sample materials of interest, such as DNA, have a tendency to adhere to cellophane membranes. A known apparatus for electro-concentrating DNA without it contacting a membrane is the so-called "salt trap".

A salt trap contains a region of high concentration(ca 7 molar) of a salt such as ammonium acetate. This salty region has a first end in electrical contact to a first polarity of a source of potential. A much less concentrated buffer solution containing the material or sample to be concentrated overlaid above the second end of the salty region. The highly concentrated salt solution is more dense than the less concentrated buffer solution, so the latter floats stably above the denser soluton below it. This upper solution is in electrical contact with a second polarity of potential. The usual arrangement of a salt trap is to have the dense solution located in the bottom of a "U" tube. One arm of the "U" tube is under the dilute buffer containing the sample to be concentrated. The second electrical contact is made to the dilute buffer. The other arm of the "U" tube is submerged in a surrounding tank of low density buffer which makes the first electrical contact.

When a voltage of proper polarity to applied between suitably arranged electrodes, charged sample migrates into the top of the concentrated solution in the side of the "U" tube under the sample-containing buffer. To maintain local conservation of charge, ions of the dense salt solution migrate out the other end of "U" tube. Since the salt solution in the "U" tube is concentrated, a large amount of sample will migrate into the trap before any of it starts to migrate out the other end. However, this U-tube arrangement is inconvenient because it requires careful technique to remove the dense solution and sample from the "U" tube without disturbing hydrostatic equilibrium with respect to the overlying buffers, and thereby losing some of the sample.

In FIG. 16, there is shown a salt trap 205 that is easy to use for any common application and is particularly adaptable to be used as part of the fraction collector 21 (FIG. 1). It eliminates the need for hydrostatic equilibrium to maintain the position of the concentrated salt "trapping solution".

In this embodiment, the fraction collector includes the capillary electrophoresis tube 30 and a salt trap composed of elements a well 630A, a well 630B, a semipermeable membrane 630C, a semipermeable membrane 630D, a narrow bore 630F, a bridge 630G and a cone bottom 630H. The membrane assembly 630D is composed and assemblied similarly to the assembly 430D in FIG. 9. The semipermeable membrane (e.g. cellophane) in membrane assembly 630D supports a concentrated salt solution (dark shading) in narrow bore 630F. This salt solution does not fill the bore. An example of such concentrated solution is 7 molar ammonium acetate.

Above bore 630F is well 630A with cone bottom 630H which contains dilute buffer solution, which is the same as in the capillary tube, e.g. 0.01 molar tris acetate buffer. Because the upper, dilute, solution is less dense than the lower, concentrated, solution; the upper solution stably floats above the lower solution.

Since the lower solution does not fill the bore 630F, it does not diffuse significantly into the lighter solution in well 630A. During fraction collection a sample zone of interest is eluted or discharged from capillary tube 30 into the dilute buffer solution in well 630A. Fraction collection occurs in a manner similar to that indicated in regard to FIGS. 7 and 8, except that the "waste" position is with the capillary tube 30 immersed in electrolyte 450 instead of electrolyte 451.

Advantageously, the solution in well 630A is same composition and concentration as the buffer electrolyte in the capillary tube 30. The solution in well 630B can be the same as in well 630A. The electrolyte solution 450 in carrier 411 advantageously is the same as in capillary tube 30. The solution 450 in carrier 411 should be the same as the electrolyte solution in capillary 30, because in the capillary tube waste position 30C, the capillary tube is immersed in the solution 450.

The electrolyte solution 451 in carrier 411 should be the same as the concentrated solution in the bore 630F. This prevents diffusion across the semipermeable membrane at the bottom of the bore 630F. If solution 451 were less concentrated, diffusion would decrease the salt concentration above the membrane, at the bottom of the bore. Such salt diffusion would decrease the effectiveness of the salt trap, especially as the resultant decreased density of the solution above the membrane can cause hydrostatic instability due to the production of a negative density gradient in the bore 630F.

In FIG. 17, there is shown a concentration of sample into the salt trap after fraction collection into buffer in well 630A. Operation proceeds similarly to that described for FIG. 15. The electrolyte level in the cup 630 is raised to level 630E above bridge 630G to provide electrical continuity. This electrolyte should have the same composition as the electrolyte in wells 630A and 630B. The polarity of the voltage applied to the electrodes is shown reversed from FIG. 15, as DNA is usually negatively charged.

Alternatively, concentration may be effected by using switch 201A-201B which is shown in FIG. 16 as well as FIGS. 7 and 8. This switch may be used to introduce the potential difference between electrolyte buffers 451 and 452. This allows concentration of the sample without removal of carrier from 411 from the apparatus of FIG. 1. It also permits filling the sample cup 630 above the bridge 630 while electrophoresis.

In operation, the separated sample (DNA or other material) migrates from well 630A, and is guided by cone bottom 630H down into the concentrated salt solution in bore 630F, where it trapped similarly in principle to that in the known "U" tube salt trap. It is trapped before reaching the semipermeable membrane in assembly 630D, so it can neither adhere to, nor pass through, the membrane. The sample and trapping solution in bore 630A can be removed later with a micropipette. It is advisable to remove the cup 630 from the carrier 411 and place it on a firm surface to avoid puncturing the membrane with the micropipette. After this operation, the sample may be treated in any way similar to that for sample removal from concentrated salt solution which has resided in a conventional salt trap. Ethanol precipitation of DNA is an example of such treatment.

Another trapping technique useful for the purposes of this invention is solid phase extraction. It may be particularly useful in micellar capillary electrophoresis. In solid phase extraction, a particulate packed bed traps analate from its solution. The bed material is chosen so that it interacts with the analate more strongly than the solvent interacts with the analate. Also, the bed material should interact weakly with the solvent in which the analate is dissolved or suspended.

Because of these interactions, the analate is removed from the solvent and becomes trapped on the surface of the bed particles. The concentrated analate is eluted later from the bed particles with a second solvent which interacts strongly with both the bed material and the analate. Preferably, the second solvent should be miscible with the original solvent and readily displace the first solvent from pores in the particles of bed material. Many types of bed material are useful.

A material consisting of $C_{18}$ hydrocarbon bonded to porous silica particles has wide application. The particles may be on the order of 100 micrometers in diameters. The solid phase extraction trapping technique is well known. An example of a review article on this topis is G. A. Junk, "Synthetic Polymers for Accumulating Organic Compounds from Water", *Organic Pollutants in Water . . . Sampling, Analysis, and Toxicity Testing,* American Chemical Society Advances in Chemistry Series, 214 (1984). Solid phase extraction de vices for liquid chromatography sample clean-up are well-known and are commercially available from a number of suppliers, for the example the Bond ElutR units available from Analytichem International Inc., Harbor City, Calif. These units are available with a large variety of packing bed materials for various applications.

Figure 18:
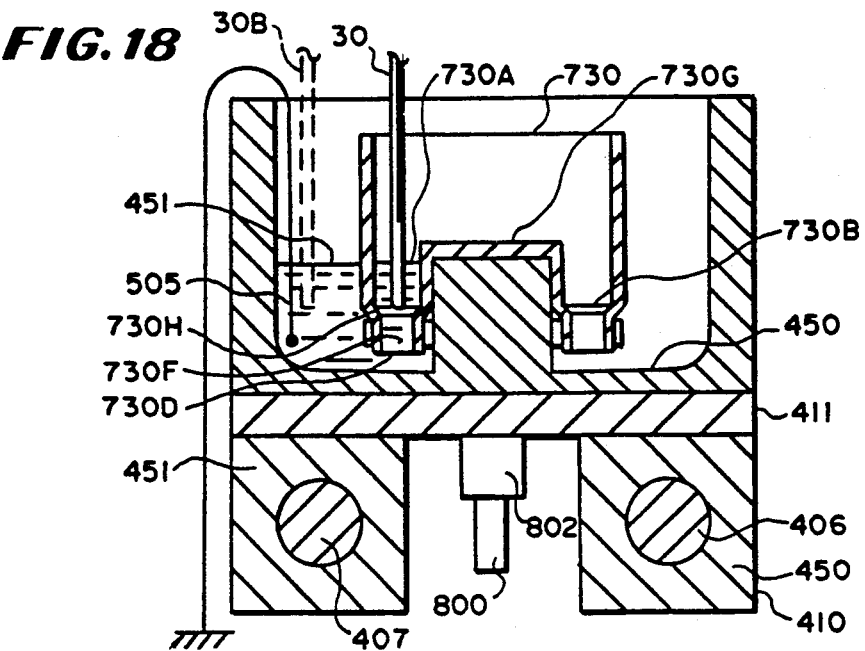
FIG. 18 is a fragmentary schematic sectional view of another embodiment of sample collecting and concentrating cup is a part of FIG. 7, altered to include solid phase extraction for fraction collection.

In FIG. 18, there is shown a sectional view of a fraction collector using a solid phase extraction trap, having a cup 730 and a carrier 411. The amount of buffer 450, if any, is insignificant in amount and does not reach any part of cup 730. Separated analate leaves capillary 30 and goes into the buffer in well 730A, with electrical continuity, provided by the path through particulate bed 730F, membrane filter assembly 730D, buffer electrolyte 451 and grounded electrode 505.

A membrane filter is used in assembly 730D instead of a semi-permeable membrane. The membrane filter in assembly 730D has relatively large pores, just small enough to prevent the particles in the bed 730F from passing through it. It provides easy passage for liquid as well as ions. During periods between fraction collection, the capillary moves to position 30B and discharges waste materials into electrolyte 451.

After fraction collection, the separated analate in well 730A is first trapped in, and then eluted from, the particulate packing bed 730F as follows: The cup 730 is removed from the carrier 411. Upon removal, the buffer containing the separated analate in the well 730A is funneled by conical surface 730H into the particulate bed 730F. The buffer flow through the bed, passes through the membrane filter at 730D; and drips to waste from the bottom surface of the filter. However, the separated analate is trapped on the surface of the particles in the bed.

Figure 19:
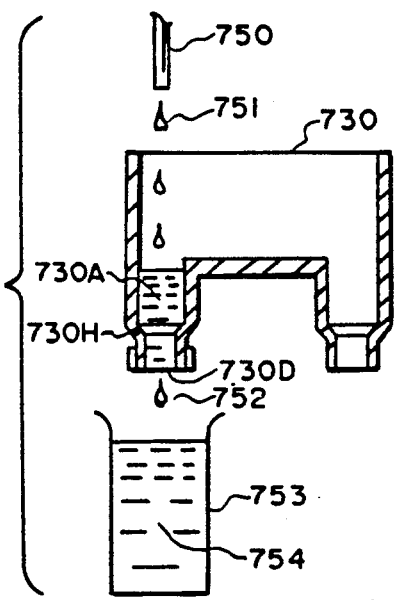
FIG. 19 is a fragmentary schematic sectional view of another embodiment of sample collecting and concentrating cup as connected for the elution of trapped sample from the solid phase extraction.

In FIG. 19, there is shown a diagrammatic drawing of a solid phase trap in which the buffer is held in the bed by the viscious friction forces due to its passage through the bed and may be flushed from the bed by refilling the well 730A with distilled water from a pipette 750. This wash water goes to waste and it is not necessary to collect it as it drops (752) from the membrane filter at 730D. The trapped analate is then eluted from the bed with an appropriate second solvent as indicated earlier. Methanol or acetonitrile solutions are examples of eluting solvents that are useful for certain applications with a $C_{18}$ bonded phase particle bed. The eluting solvent is pipetted (750) into well 730A, where it removes the analate from the bed, passes through the membrane at 730D carrying the analate with it, and drips into receiving vessel 753. Preferably, the eluting solvent is volatile enough so that the contents 754 can easily be evaporated to provid a concentrated analate.

Figure 20:
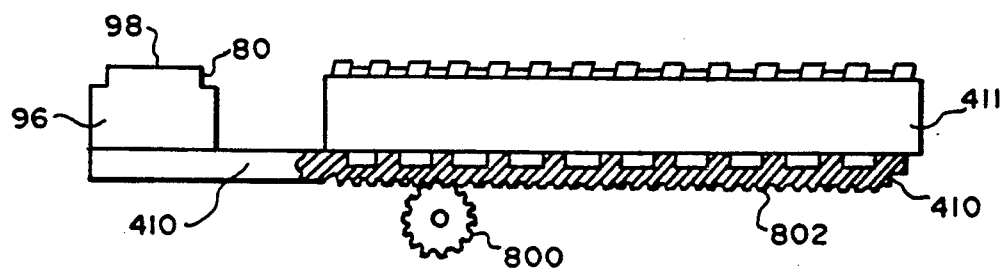
FIG. 20 is a side elevational view of a fraction collector used in an embodiment of the invention in forming a part of FIG. 1.

In FIG. 20, there is shown an elevational view of the carrier 411, plate 410, a pinion 800 and the vacuum vessel assembly 80 mounted together with the pinion 800 positioned to drive the plate 410 together with the removable carrier 411 and the fixed vacuum vessel assembly 80.

The vacuum vessel assembly 80 includes a vacuum vessel holder 96 mounted to the plate 410 and the removable cap 98 connected by hoses to a source of vacuum as described above and adapted to apply vacuum pressure to the capillary tube 30 (FIG. 1) for the purpose of sample injection.

The plate 410 supports the carrier 411 which may be removed for concentrating effluent within it or replaced to continue operations while the concentration is going on or for any other reason. They are all driven together by the pinion 800 which engages the rack 802 in the center of the block 410 to incrementally one cell at a time move the carrier 411 over the capillary tube so that it may be inserted into buffer solution therein for removal of either waste or for extraction of separated molecular species.

Before operating the capillary electrophoresis apparatus, the capillary tube 30 should be arranged as shown in FIG. 1. Samples to be separated should be placed in sample tubes on sample holding reel 44. Electrolyte buffers suitable for the separation placed in electrolyte vessels 60A, 60B, 60C and 96. Sample concentrating cells are placed in a carrier 411, buffer added and the carrier loaded on a block 410 at the first collection position.

The apparatus is preferably operated under the control of a conventional programmed controller or computer but may be operated by hand. In operation, if the proper buffer electrolyte is not already in the capillary tube 30, the movable arm 46 puts the end of the capillary tube 30 in the desired buffer vessel 60A, 60B or 60C and an external control signal on conductor 116 activates pressure control solenoid valve 88 putting a partial vacuum in the buffer reservoir by connecting it through tubes 94 and 114 to low-pressure vacuum tank 84. This pulls buffer from vessel 60A, 60B or 60C into the capillary tube 30, and into vessel 96, completely filling the capillary tube 30. Advantageously, the pressure sensor 104 should be programmable so that different degrees of reduced pressure or partial vacuum may be preset in the tank by the external controller or computer (not shown).

It is desirable that a higher vacuum be used to rapidly fill the tube and a lower vacuum be used to more slowly pick up a minute amount of sample. A typical higher vacuum is 500 centimeters of water or about one-half of an atmosphere. A typical lower vacuum is 12 inches of water. When it is desired to effect a separation, the vertical section of the capillary tube 30 dips into a sample tube such as 58A or 58B on sample holding reel 44. A minute amount of sample is withdrawn into the capillary tube 30 by the application of negative pressure on electrode buffer vessel 96.

When pressure control solenoid valve 88 operates to reduce the pressure in electrode buffer vessel 96, the pressure does not reduce instantaneously. This can cause an error in the sample volume. Since the bore of the capillary tube 30 is very small, uinder 100 micrometers, the flow induced by pressure differences of less than one atmosphere results in laminar flow; flow of a rate which is proportional to the pressure (transitional and turbulent flow result in flow rates that are not directly proportional to pressure). The volume of sample taken up therfore is proportional to the time integral of the flow rate.

Since flow rare is proportional to pressure, the volume of the sample is therefore also proportional to the time integral of the negative gauge pressure within the electrode buffer vessel 96. Pressure sensor 104 monitors the negative gauge pressure within electrode buffer vessel 96 and transmits it through electrical lead 92 to electrical interface 82 and thence to an external controller or computer through lead 106. The external computer can operate the pressure control solenoid valve 88 for a fixed time to reduce the pressure in vessel 96 while accumulating the integral of the reduced pressure and thereby tabulate sample volumes for display or for correction of peak data. In the preferred embodiment, the controller operates the solenoid valve 88 to pick up sample and simultaneously monitors the accumulating integral. When the integral reaches a preset value, the controller de-energizes the solenoid valve. This has been found to provide very reproducible sample pickups that correspond to a predetermined amount.

A refinement of this preferred embodiment requires picking up a calibrating or "dummy" sample in the same manner as in the preferred embodiment. In this case, the controller measures the accumulating integral and de-energizes the valve upon reaching the preset value of integral, but also measures the final value of the integral upon pressure equilibrium after the valve 88 is de-energized. The difference between the preset integral and the final value of the integral represents an error that is corrected by subtracting this error from the preset value to form a corrected preset value.

Further sample pickups are made using the preferred embodiment with the corrected preset value. These samples accurately correspond to a predetermined amount. Another alternative is for the controller to be programmed to iteratively determine the proper energization time of pressure control solenoid valve 88 to cause the sample to correspond to a predetermined amount.

After a sample is taken up into the end of the capillary tube 30 (only a very small amount of sample is taken up, often on the order of a nanoliter), movable arm 46 moves the end of the capillary tube 30 into one of the buffer vessels 60A, 60B or 60C. The high voltage power supply 14 is turned on, preferably also by automatic means, the manifold 301 is operated to apply potential and the fraction collector starts in the waste position. The sample starts to migrate and separate in the capillary tube 30 in response to the potential across the capillary tube.

Figure 21:
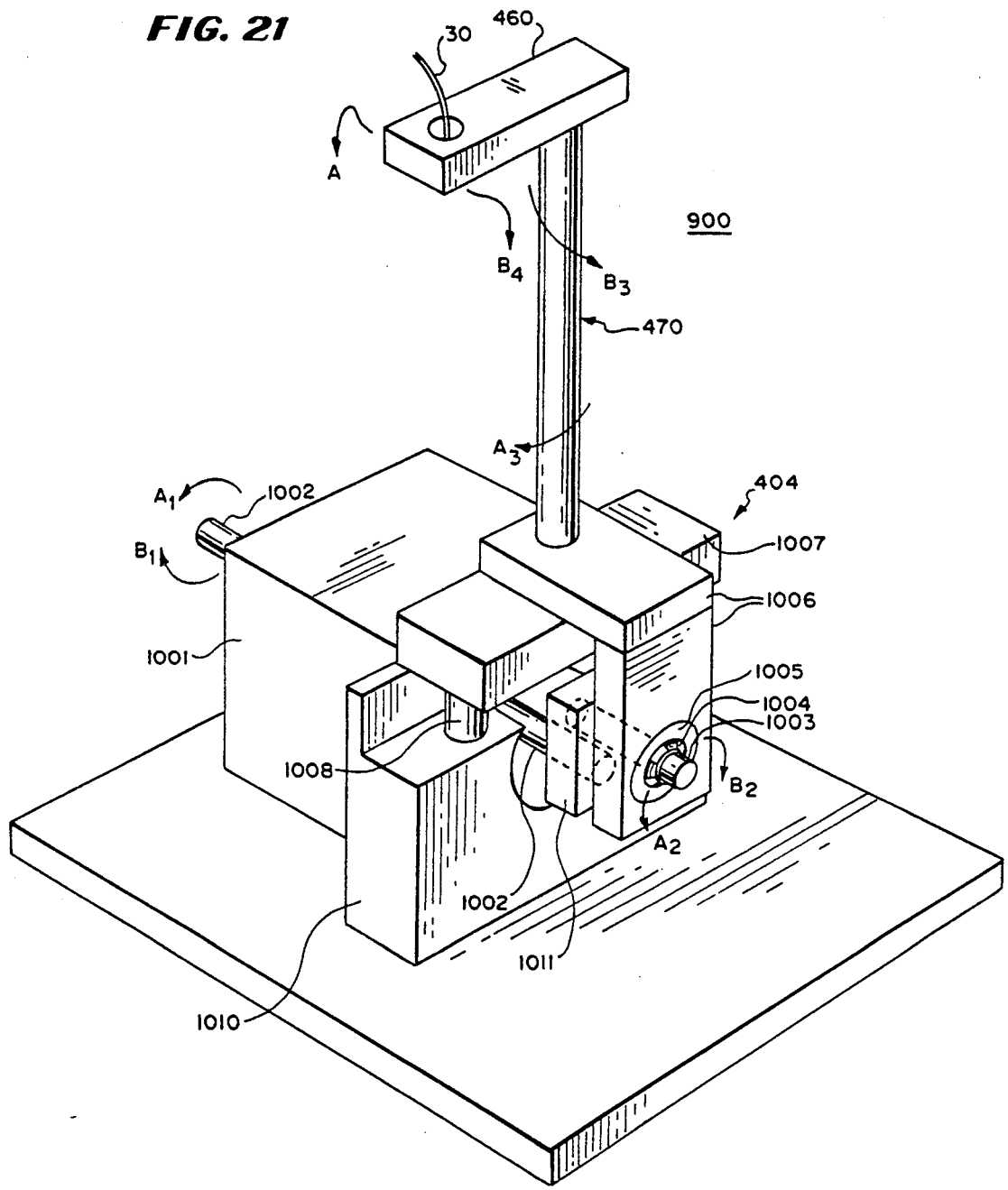
FIG. 21 is an isometric view of a portion of the fraction collector of FIG. 1.

In FIG. 21, there is shown a perspective view of the lifting and rotating rod assembly 906 having the lifting and rotating mechanism 404 for moving the lifting and rotating rod 470 vertically and rotating it for the purpose of positioning the capillary rube 30 (FIG. 1). The lifting and rotating rod assembly 900 is composed of lifting and rotating rod 470, and lifting and rotating mechanism 404 which includes a stepping motor 1001 with shaft 1002, crank arm 1011, crank rod 1003, bearing 1004 with spherical outside diameter and cylindrical hole to receive the crank rod with a slip fit to allow relative rotating and sliding motion between the rod and the hole, bearing retainer 1005 with spherical recess for retaining the bearing 1004, operating arm 1006 rigidly fastened to rod 470, support block 1001 supported by guide rods 1008 and 1009 (not visible on FIG. 21) which slide in guide block 1010.

The spherical recess in bearing retainer 1005 retains the bearing 1004 with close spherical contact. Spherical bearing 1004 is free to wobble rotatively at any angle within retainer 1004, but it cannot move translatively within retainer 1004.

The arm 460 is shown in its uppermost postion in FIG. 21 halfway between the two downmost positions. It can be seen that if motor shaft 1002 rotates in direction A, the crank rod 1003 moves in direction A2, the bearing 1004 swings to the left and down, lifting and rotating rod 470 rotates and lowers in direction A3 and the end of the arm 460 which bears the capillary tube 30 swings to the rear and downward shown as A4.

If the motor shaft rotates in direction B, rod 1003 moves in direction B2. The bearing 1004 swings to the right and down, rod 470 rotates and lowers in direction B3 and arm 460 moves capillary tube 30 in the direction B4. It has been found that good capillary positioning action results when the shaft 1002 of the stepper motor 1001 is stepped about 120 degrees in each direction from high center. This is a total rotation of 240 degrees from one full-down position of the capillary to the other full-down position.

Figure 22:
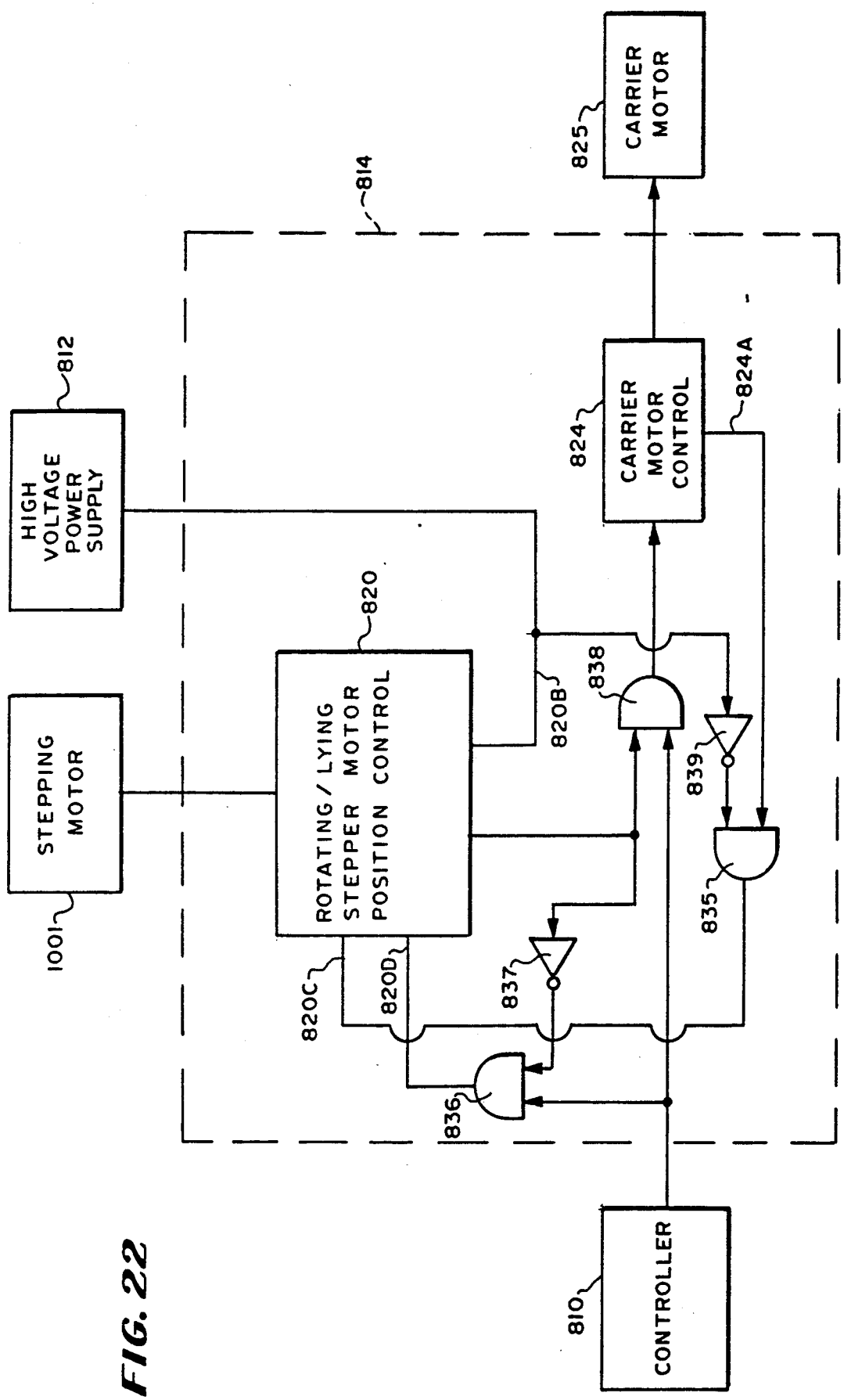
FIG. 22 is a block diagram of a system for controlling fraction collecting.

In FIG. 22, there is shown a block diagram of circuitry used to index the carrier 411, to control the lifting and rotating arm 460, and to apply power to the capillary 30 in such a manner as to cooperate with the automatic collection of fractions from the capillary 30 during electrophoresis. This circuit includes a controller 810, a circuit 812 for applying voltage from the power supply across the buffer solutions in the fraction collector and the electrophoresis tube to perform separation by electrophoresis and collection into the fraction collector and a circuit 814 for moving the carrier 411 to position a selected one of the sample concentrator cups 412-488 for receiving a selected effluent sample or waste material and for positioning the end of the capillary tube 30 either to deposit effluent in the buffer solution or sample into a concentrating cell.

The controller 810 may be any unit capable of generating pulses which distinguish between a band passing through the sensor, solvent without a band, and a time delay to compensate for the time it takes for a band leaving the sensor to reach the end of capillary tube 30. It may incorporate a cycling timer to generate pulses at regular time intervals. This controller may be as simple as that disclosed in U.S. Pat. No. 3,202,188 to Robert William Allington, granted Aug. 24, 1965, or as complicated as many of the programmable computer controller used today which receive sensed signals and provide outputs programmed to collect multiple zones or to collect multiple zones or to collect zones from electrophoresis in any selected pattern.

To control the lifting and rotating arm 460 and the lifting and rotating rod 470, the control circuit 814 includes rotating lifting stepper motor position control circuit 820, a carrier motor control circuit 824, and AND gates such as 835, 836 and 838 to provide proper circuit logic. These circuits are arranged so that after a peak is detected, a signal is applied to gate 836 which activates counterclockwise movement of the stepper motor 1001 through the input 820D of its control circuit 820.

The stepper motor 1001 lifts and rotates the lifting and rotating rod 470 which lifts and rotates the lifting and rotating arm 460 holding the capillary tube 30 so that the carrier motor 825 which is started a short time later can index the carrier 410 to the next sample cup. As soon as the lifting starts, the DOWN output 820B of control circuit 820 turns off, turning off the high voltage power supply 812. After the stepper motor 820 has rotated and completely lifted the lifting and rotating rod 470, the UP output signal on lead 820A is transmitted through inverter 837 and turns off gate 836, stopping the stepper motor in its UP position. Simultaneously, the signal on lead 820A is ANDed in gate 838 with the signal from the controller 810. The output of gate 838 is transmitted to carrier motor control 824 which turns on carrier motor 825 to bring the next sample cup into position. The carrier motor stops at the next tube and the STOP output on lead 824A of carrier motor control 824 causes AND gate 835 to activate clockwise movement of stepper motor 1001 (FIG. 21) through its control circuit 820. This rotates and lower the capillary tube 30 in arm 460 back to the next sample cup. When the arm is all of the way down, the DOWN output 820B from the control 820 goes on and turns off AND gate 835 through inverter 839. The resulting output of gate 835 stops the lowering of the arm 460 by turning off the clockwise input (CW) 820C of control 820, and stopping the stepping motor 1001.

In operation, the lift and rotate arm assembly 900 is moved under the control of the controller 810 (FIG. 21) to the vacuum vessel shown at 98 (FIG. 1) and the other end is moved to a sample and vacuum draws a sample into the end of the electrophoresis tube, after which the controller 810 causes the arm 46 to move one end of the capillary tube 30 to a buffer and the arm assembly 900 moves the other end into position for electrophoresis within the buffer 451 in the carrier 411 and the power is turned on. With the power on, electrophoresis takes place until a zone containing a sample is selected and then the rod assembly 900 moves the arm 460 to which the end of the capillary tube is attached to insert the end of the capillary rube into the first sample collecting cell where the sample is collected. After collecting the sample, the arm is moved back into the buffer until the next zone is detected at which time, the fraction collector may be moved into position for depositing the next separated zone in a new sample cell or, if appropriate programming is provided, into the same cell until a certain number of peaks have been collected in the cell. After the zones have been electrophoresed, the carrier may be removed and potential applied to the buffer to concentrate the samples in the sample cells.

More specifically, when the sensor 72 (FIG. 1) detects a zone, the controller 810 (FIG. 22) applies a signal through the AND gate 836 to the stepping motor position control 820, which rotates motor 1001 counterclockwise, swinging crank rod 1003 to turn and raise the arm 460 (FIG. 21).

As the lift arm assembly 900 is lifting the end of the capillary tube 30 (FIG. 1), the signal is also applied to the high voltage power supply 812 to turn off the high voltage power. After the assembly 900 has rotated the arm back over and into the next cell advanced by the carrier, the stepper motor 1001 is stopped by the reapplication of the DOWN signal on lead 820B to the AND gate 835, which shuts off the CW input of the stepper motor control 820. At the same time, the DOWN signal is applied to the power supply to reapply power and electrophores the zone into the sample cup.

In one embodiment, the sample cell is a concentrator having a membrane over one well and the zone is deposited over that well. Power is applied through the buffer solution in the carrier to continue electrophoresis into that cell while the liquid level is below the bridge of the concentrator cell to prevent it from flowing across to the other side until the concentrating step.

In another embodiment, the sample cell is a salt trap and in still another embodiment, the sample cell is a solid phase trap. In both of these embodiments, the separated sample, is layered on top of a dense liquid or held by a capillary zone away from the membrane until further concentrating.

After the electrophoresis of the entire sample into zones and collecting, the carrier 411 may be removed and potential applied across it to concentrate the samples. When this happens in the membrane concentrator embodiment, the buffer fluid must extend slightly over the bridge of the sample cells to permit ionic conduction over the bridge so the sample can be concentrated against the membrane. Similarly, in the salt trap, the sample is concentrated in a heavy layer by a potential applied across the trap.

The separated sample zones migrate through the sensor 72, are recorded by the absorbance monitor and trigger the fraction collector 21 to move the end of the capillary tube to a sample collection cell.

When the separation is complete, sample holding reel 44 rotates one tube position, movable arm 46 moves the end of the capillary tubing 30 from the electrode buffer vessel 96 into the next sample tube, and the operation cycle repeats for the next sample. It should be noted that the buffer vessels must be filled with the same height and the electrode vessel buffer 80 must be vented to the atmosphere (pressure control solenoid valve 88 de-energized) during electrophoretic separation. If this precaution is not taken, buffer electrolyte will flow by siphon action through the capillary tube 30. This is undesirable since siphon flow within the capillary tube 30 has a laminar flow profile that induces axial mixing of the sample zones and degrades the resolution of the separation.

From the above description, it can be understood that the separating apparatus of this invention has several advantages, such as for example: (1) a high degree of sample introduction accuracy is possible because of integration of the vacuum level during sampling; (2) separated sample bands may be quantitatively collected with minimal dilution; and (3) collected sample may be reconcentrated without significant loss and without removal from the collecting vessel.

Although a preferred embodiment of the invention has been described with some particularity, many modifications and variations are possible in the preferred embodiment in the light of the above teachings. Therefore, it is to be understood that, within the scope of the appended claims, the invention may be practiced other than as specifically described.

What is claimed is:

1. Apparatus for detecting bands having a predetermined direction of motion in a separation medium comprising:
    a light source;
    a light detector adapted to provide signals indicating bands;
    a capillary tube means for holding the separation medium;
    means for positioning said light source and light detector on differing sides of said separating medium, wherein a predetermined volume of said separating medium between said light detector and light source is subject to detection;
    said predetermined volume being less than 100 nanoliters;
    means for injecting sample in a first end of said capillary tube;
    means for applying a potential across the separation medium;
    collection and trapping means adapted to receive different bands in correspondingly different compartments;
    means for moving at least a portion of the collection and trapping means and one end of the capillary tube with respect to each other in response to said signals;
    certain of the different compartments having a volume of between 20 nanoliters and two milliliters;
    said means for applying a potential including electrode manifold means having a plurality of removable platinum wire electrodes attached to it, and a corresponding number of buffer electrolyte containers, wherein said electrodes are electrically connectable to said buffer beaker.

2. Apparatus according to claim 1 further including a mounted grounding clapper released by an electromagnet located below the mounting surface to act as a safety ground by swinging against the electrically conducting electrode manifold when overhead access lid is opened, the grounding clapper incorporating a resistive path to ground.

3. Apparatus according to claim 2 in which the collection means includes a carrier means, said injection means includes a controllable-pressure vessel means; said apparatus further including a support means, means for moving the support means horizontally, slideably, on guide means, said capillary tube being connected to a removable cap means covering the controllable-pressure vessel means.

4. Apparatus according to claim 3 in which said collection means includes a lifting and rotating arm means and a lifting and rotating rod means.

5. Apparatus according to claim 4 in which said injection means includes a sealing piece means in the shape of a frustum of a cone sized to make a seal with conical hole in cap means when arm is lowered on said pressure vessel means; said vessel having a vacuum applied to it through flexible connecting tubing for initially filling the capillary tube with electrolyte and for loading sample into the capillary tube.

6. Apparatus for detecting bands having a predetermined direction of motion in a separation medium comprising:
    a light source;
    a light detector adapted to provide signals indicating bands;
    a capillary tube means for holding the separation medium;
    means for positioning said light source and light detector on differing sides of said separating medium, wherein a predetermined volume of said separating medium between said light detector and light source is subject to detection;
    said predetermined volume being less than 100 nanoliters;
    means for injecting sample in a first end of said capillary tube;
    means for applying a potential across the separation medium;
    collection and trapping means adapted to receive different bands in correspondingly different compartments;
    means for moving at least a portion of the collection and trapping means and one end of the capillary tube with respect to each other in response to said signals;
    said collection means including a carrier means that holds a number of sample collection cups and a grounding electrode adapted to be immersed in a conducting electrolyte in electrical contact with electrolyte buffer in the cup;
    the sample collection cup having two wells adapted to contain electrolyte.

7. Apparatus according to claim 6 in which bottoms of the wells are covered with clamped-on semipermeable membrane assemblies to permit the flow of buffer ions but not the migration of separated sample.

8. Apparatus according to claim 7 wherein the said membrane is made of a fine-pored, relatively uncharged materials such as cellophane.

9. Apparatus according to claim 8 in which said salt traps include high concentration of a salt having a first end in electrical contact to a first polarity of a source of potential provided by much less concentrated buffer solution containing the material or sample to be concentrated overlaid above the second end of the salty region; said highly concentrated salt solution being more dense than the less concentrated buffer solution, so the latter floats stably above the denser solution below it; said upper solution being in electrical contact with a second polarity of potential.

10. Apparatus according to claim 7 wherein the membrane is a specific-ion transmitting membrane.

11. Apparatus according to claim 7 in which each sample cup has a connecting bridge between the two wells which provides fluid and electric connection between wells if the electrolyte level is sufficiently high but prevents it if either the level of the electrolyte or buffer in the wells is lower than the height of the bridge.

12. Apparatus according to claim 11 in which the carrier means is supported by a support plate which is supported by bearing blocks which rides on support rods.

13. Apparatus according to claim 12 in which lifting and rotating means lifts arm means to effect this withdrawal of said capillary tube end above the top of the carrier means; conventional indexing means for moving the support plate whereby the next sample collection cup is moved into position for fraction collection, or the conical hole in the removable cap is moved into position under the capillary tube for injection of the next sample.

14. Apparatus according to claim 13 in which the arm has first and second rotational positions; said collection means includes means to move from the collecting position to the waste position; said means including the arm first is lifted by the rotating and lifting mechanism and rotates to the waste position of the capillary tube when no material of preparative interest is coming out of the capillary tube for discharge into the buffer residing in carrier and the sample injection position for the arm and capillary tube and in electrolyte residing in the other side of the carrier.

15. Apparatus according to claim 14 in which the sample cup has a key molded into it, under the lower surface of bridge; said key fitting into one of the several slots and being sized and spaced such that sample cups are located close together and accurately positioned within carrier means, whereby the indexing mechanism that moves the carrier means along guides can accurately position the sample cups under the capillary tubing.

16. Apparatus according to claim 14 in which the sample cups are fastened together; said carrier having one locating or keying feature used for each group of fastened-together sample cups.

17. Apparatus for detecting bands having a predetermined direction of motion in a separation medium comprising:
a light source;
a light detector adapted to provide signals indicating bands;
a capillary tube means for holding the separation medium;
means for positioning said light source and light detector on differing sides of said separating medium, wherein a predetermined volume of said separating medium between said light detector and light source is subject to detection;
said predetermined volume being less than 100 nanoliters;
means for injecting sample in a first end of said capillary tube;
means for applying a potential across the separation medium;
collection and trapping means adapted to receive different bands in correspondingly different compartments;
mean for moving at least a portion of the collection and trapping means and one end of the capillary tube with respect to each other in response to said signals;
said collection means including a carrier means that holds a number of sample collection cups and a grounding electrode adapted to be immersed in a conducting electrolyte in electrical contact with electrolyte buffer in the cup;
the sample collecting cells being salt traps.

18. Apparatus according to claim 17 in which said salt traps include high concentration of a salt having a first end in electrical contact to a first polarity of a source of potential provided by much less concentrated buffer solution containing the material or sample to be concentrated overlaid above the second end of the salty region; said highly concentrated salt solution being more dense than the less concentrated buffer solution, so the latter floats stably above the denser solution below it; said upper solution being in electrical contact with a second polarity of potential.

19. Apparatus according to claim 18 in which the dense solution is located in the bottom of a "U" tube; one arm of the "U" tube is under the dilute buffer containing the sample to be concentrated; the second electrical contact is made to the dilute buffer; the other arm of the "U" tube is submerged in a surrounding tank of low density buffer which makes the first electrical contact.

20. Apparatus according to claim 17 in which a salt trap includes a first membrane assembly adapted to support a concentrated salt solution in a narrow bore; a well with cone bottom which contains dilute buffer solution; said upper solution stably floating above the lower solution; the lower solution does not fill the bore; said means for rotation and lifting including means for discharging the zone of interest from capillary tube into the dilute buffer solution in well.

21. Apparatus for detecting bands having a predetermined direction of motion in a separation medium comprising:
a light source;
a light detector adapted to provide signals indicating bands;
a capillary tube means for holding the separation medium;
means for positioning said light source and light detector on differing sides of said separating medium, wherein a predetermined volume of said separating medium between said light detector and light source is subject to detection;
said predetermined volume being less than 100 nanoliters;
means for injecting sample in a first end of said capillary tube;
means for applying a potential across the separation medium;
collection and trapping means adapted to receive different bands in correspondingly different compartments;
means for moving at least a portion of the collection and trapping means and one end of the capillary tube with respect to each other in response to said signals;
said collection means including a carrier means that holds a number of sample collection cups and a grounding electrode adapted to be immersed in a conducting electrolyte in electrical contact with electrolyte buffer in the cup;
the sample cells being solid phase extraction cells.

22. Apparatus according to claim 21 further including a particulate packed bed means fur trapping analate from its solution, said bed material being selected to interact with the analate more strongly than the solvent interacts with the analate.

23. Apparatus according to claim 21 in which the bed material interacts weakly with the solvent in which the analate is dissolved or suspended.

24. Apparatus according to claim 23 in which the bed material includes $C_{18}$ hydrocarbon bonded to porous silica particles; said particles may be on the order of 100 micrometers in diameter.

25. Apparatus according to claim 21 in which separated analate leaves the capillary tube going into the buffer in a well in the cup, with electrical continuity provided by the path through particulate bed, membrane filter assembly, buffer electrolyte and grounded electrode; a membrane filter supporting the bed having relatively large pores, just small enough to prevent the particle in the bed from passing through it, whereby it provides easy passage for liquid as well as ions.

26. A fraction collector for electrophoresis comprising:
a capillary electrophoresis means;
an electrophoretic high voltage electrical circuit;
means for completing the electrophoretic high voltage electrical circuit;
an electrically conductive trapping means for trapping the sample of interest;
the electrically conductive trapping means including a semipermeable membrane.

27. A fraction collector for electrophoresis comprising:
a capillary electrophoresis means;
an electrophoretic high voltage electrical circuit;
means for completing the electrophoretic high voltage electrical circuit;
an electrically conductive trapping means for trapping the sample of interest;
the trap including an ion selective membrane.

28. A fraction collector for electrophoresis comprising:
a capillary electrophoresis means;
an electrophoretic high voltage electrical circuit;
means for completing the electrophoretic high voltage electrical circuit;
an electrically conductive trapping means for trapping the sample of interest;
the trap including a solid phase extraction trap.

29. A reaction collector for electrophoresis comprising:
a capillary electrophoresis means;
an elecrophoretic high voltage electrical circuit;
means for completing the electrophoretic high voltage electrical circuit;
an electrically conductive trapping means for trapping the sample of interest;
being a salt trap.

30. Apparatus for detecting bands having a predetermined direction of motion in a separation medium comprising:
a light source;
a light detector adapted to provide signals indicating bands;
a capillary tube means for holding the separation medium;
means for positioning said light source and light detector on differing sides of said separating medium, wherein a predetermined volume of said separating medium between said light detector and light source is subject to detection;
said predetermined volume being less than 100 nanoliters;
means for injecting sample in a first end of said capillary tube;
means for applying a potential across the separation medium;
collection and trapping means adapted to receive different bands in correspondingly different compartments;
mean for moving at least a portion of the collection and trapping means and one end of the capillary tube with respect to each other in response to said signals;
said collection means including a carrier means that holds a number of sample collection cups and a grounding electrode adapted to be immersed in a conducing electrolyte in electrical contact with electrolyte buffer in the cup;
a sample injector;
said sample injector including a vacuum source; a source of samples; and a vacuum chamber;
said vacuum chamber communicating with one end of a separating means;
said separating means having a second end which communicates with a sample source;
means for causing a vacuum in said vacuum chamber to draw sample from said source of sample wherein sample is pulled at a slow rate into said second end of the separating means; and
pressure measuring means adapted to measure the pressure in said vacuum chamber and generate a signal indicative thereof;
said signal causing a connective means to increase the accuracy of quantitative results obtained from said sample.

31. Apparatus for detecting bands having a predetermined direction of motion in a separation medium comprising:
a light source;
a light detector adapted to provide signals indicating bands;
a capillary tube means for holding the separation medium;
means for positioning said light source and light detector on differing sides of said separating medium, wherein a predetermined volume of said separating medium between said light detector and light source is subject to detection;
said predetermined volume being less than 100 nanoliters;
means for injecting sample in a first end of said capillary tube;
means for applying a potential across the separation medium;
collection and trapping means adapted to receive different bands in correspondingly different compartments;
means for moving at least a portion of the collection and trapping means and one end of the capillary tube with respect to each other in response to said signals;
said collection means including a carrier means that holds a number of sample collection cups and a grounding electrode adapted to be immersed in a conducting electrolyte in electrical contact with electrolyte buffer in the cup;
said sample collecting cells being salt traps.

32. Apparatus according to claim 31 in which said salt traps include high concentration of a salt having a first end in electrical contact to a first polarity of a source of potential provided by much less concentrated buffer solution containing the material or sample to be concentrated overlaid above the second end of the salty region; said highly concentrated salt solution being more dense than the less concentrated buffer solution, so the latter floats stably above the denser solution below it; said supper solution being in electrical contact with a second polarity of potential.

33. Apparatus for detecting bands having a predetermined direction of motion in a separation medium comprising:
   a light source;
   a light detector adapted to provide signals indicating bands;
   a capillary tube means for holding the separation medium;
   means for positioning said light source and light detector on differing sides of said separating medium, wherein a predetermined volume of said separating medium between said light detector and light source is subject to detection;
   said predetermined volume being less than 100 nanoliters;
   means for injecting sample in a first end of said capillary tube;
   means for applying a potential across the separation medium;
   collection and trapping means adapted to receive different bands in correspondingly different compartments;
   means for moving at least a portion of the collection and trapping means and one end of the capillary tube with respect to each other in response to said signals;
   said collection means including a carrier means that holds a number of sample collection cups and a grounding electrode adapted to be immersed in a conducting electrolyte in electrical contact with electrolyte buffer in the cup;
   the sample cup having two wells adapted to contain electrolyte.

34. Apparatus according to claim 33 in which bottoms of the wells are covered with clamped-on semipermeable membrane assemblies to permit the flow of buffer ions but not the migration of separated sample.

35. Apparatus according to claim 34 in which each sample cup has a connecting bridge which provides fluid and electric connection between wells if the electrolyte level is sufficiently high but prevents it if either the level of the electrolyte or buffer in the wells is lower than the height of the bridge or the electrolyte or buffer levels in the two sides of the carrier is lower than the height of the supporting wall.

36. Apparatus according to claim 35 in which the carrier means is supported by the support plate which is supported by bearing blocks which rides on support rods after the capillary tube is withdrawn from the sample cup.

37. Apparatus according to claim 36 in which lifting and rotating means lifts arm means to effect this withdrawal of said capillary tube end above the top of the carrier means; conventional indexing means for moving the support plate whereby the next sample collection cup is moving into position for fraction collection, or the conical hole in the removable cap is moved into position under the capillary tube for injection of the next sample.

38. Apparatus according to claim 37 in which the arm has first and second rotational positions; said collection means includes means to move from the collecting position to the waste position; said means including the arm first is lifted by the rotating and lifting mechanism and rotates to the waste position of the capillary tube when no material of preparative interest is coming out of the capillary tube for discharge into the buffer residing in carrier and the sample injection position for the arm and capillary tube and in electrolyte residing in the other side of the carrier.

39. Apparatus according to claim 38 in which the sample cup has a key molded into it, under the lower surface of bridge; said key fitting into one of the several slots and being sized and spaced such that sample cups are located close together and accurately positioned within carrier means, whereby the indexing mechanism that moves the carrier means glong guide rods can accurately position the sample cups under the capillary tubing.

40. Apparatus according to claim 39 in which the sample cups are fastened together; said carrier having one locating or keying feature used for each group of fastened-together sample cups.

41. A method of performing electrophoresis comprising the steps of:
   establishing a potential across a separating medium;
   introducing a sample into the separating medium for electrophoresis through it;
   carrying an end of the medium over a fraction collection with an arm;
   positioning the arm with the capillary tube above a well in a sample cup incorporating a trap;
   lowering the arm until the capillary tube enters the electrolyte in the well of the sample cup;
   electrophoresing and or electro-osmosing material from the capillary tube into the electrolyte in the collecting well after the capillary tube has been lowered into the electrolyte in the well establishing electrical continuity;
   turning the power supply off raising the arm when the sample component of interest has been completely eluted into the well;
   rotating the arm and lowering the arm until the capillary tube dips into the electrolyte within carrier collecting waste material between collected sample zones into the electrolyte; and
   using the sample cup for concentrating the separated sample component after the electrophoretic separation.

42. A method according to claim 41 in which sample cups are stacked side by side in a carrier which has been removed from the electrophoresis apparatus;
   adding more electrolyte buffer tot he sample cups so that the electrolyte covers the bridges;
   putting electrodes in the electrolyte solutions within carrier;
   applying a potential difference of 100 to 200 volts to the electrodes so that sample molecules in wells migrate downwards to the top surface of the semipermeable membrane;
   after sufficient time has elapsed for concentration to take place, the sample cups are removed and placed vertically with the semipermeable membranes laying upon a firm surface;

concentrated sample lying just above the membrane are pipetted off.

43. A method of performing electrohporesis comprising the steps of:

establishing a potential across a separating medium;

introducing a sample into the separating medium for electrophoresis through it;

carrying an end of the medium over a fraction collection with an arm;

positioning the arm with the capillary tube above a well in a sample cup incorporating a trap;

lowering the arm until the capillary tube enters the electrolyte in the well of the sample cup;

electrophoresing and or electro-osmosing material from the capillary tube into the electrolyte in the collecting well after the capillary tube has been lowered into the electrolyte in the well establishing electrical continuity;

turning the power supply off raising the arm when the sample component of interest has been completely eluted into the well;

rotating the arm and lowering the arm until the capillary tube dips into the electrolyte within carrier collecting waste material between collected sample zones into the electrolyte;

supporting a concentrated salt solution in a narrow bore;

inserting a dilute buffer solution above the bore which is the same as in the capillary tube;

discharging a sample zone from capillary into the dilute buffer solution in the well; and concentrating sample into the salt trap after fraction collection into buffer in well.

44. A method of performing electrophoresis comprising the steps of:

establishing a potential across a separating medium;

introducing a sample into the separating medium for electrophoresis through it;

carrying an end of the medium over a fraction collection with an arm;

positioning the arm with the capillary tube above a well in a sample cup incorporating a trap;

lowering the arm until the capillary tube enters the electrolyte in the well of the sample cup;

electrophoresing and or electro-osmosing material from the capillary tube into the electrolyte in the collecting well after the capillary tube has been lowered into the electrolyte in the well establishing electrical continuity;

turning the power supply off raising the arm when the sample component of interest has been completely eluted into the well;

rotating the arm and lowering the arm until the capillary tube dips into the electrolyte within carrier collecting waste material between collected sample zones into the electrolyte;

the step of concentrating sample including the steps of: raising the electrolyte level in the cup to a level above the bridge to provide electrical continuity; applying potential with a polarity of the voltage applied to the electrodes to move the sample from well to well whereby separated sample migrates from the well and is guided by cone bottom down into the concentrated salt solution in bore, wherein it is trapped before reaching the semipermeable membrane in assembly so it can neither adhere to, nor pass through the membrane; and removing the sample with a micropipette.

45. A method of performing electrophoresis comprising the steps of:

establishing a potential across a separating medium;

introducing a sample into the separating medium for electrophoresis through it;

carrying an end of the medium over a fraction collection with an arm;

positioning the arm with the capillary tube above a well in a sample cup incorporating a trap;

lowering the arm until the capillary tube enters the electrolyte in the well of the sample cup;

electrophoresing and or electro-osmosing material from the capillary tube into the electrolyte in the collecting well after the capillary tube has been lowered into the electrolyte in the well establishing electrical continuity;

turning the power supply off raising the arm when the sample component of interest has been completely eluted into the well;

rotating the arm and lowering the arm until the capillary tube dips into the electrolyte within carrier collecting waste material between collected sample zones into the electrolyte;

trapping analate in a particulate packed bed from its solution, wherein the bed material is chosen so that it interacts with the analate more strongly than the solvent interacts with the analate and interacts weakly with the solvent in which the analate is dissolved or suspended; and eluting the concentrated analate from the bed particles with a second solvent which interacts strongly with both the bed material and the analate.

* * * * *